United States Patent [19]
Belt et al.

[11] Patent Number: 5,344,720
[45] Date of Patent: Sep. 6, 1994

[54] BISTABLE MAGNETO-OPTIC SINGLE CRYSTAL FILMS AND METHOD OF PRODUCING SAME UTILIZING CONTROLLED DEFECT INTRODUCTION

[75] Inventors: Roger F. Belt; John B. Ings, both of Rockaway Township, Morris County, N.J.

[73] Assignee: Litton Systems, Inc., Morris Plains, N.J.

[21] Appl. No.: 789,362

[22] Filed: Nov. 8, 1991

[51] Int. Cl.$^5$ .............................................. B32B 9/00
[52] U.S. Cl. .................... 428/692; 427/127; 427/129; 427/130; 428/694 GT; 428/694 ML; 428/703; 430/945
[58] Field of Search ............... 428/692, 694, 702, 900, 428/694 GT, 701, 694 ML; 252/62.51, 62.52, 62.56, 62.57, 62.58; 430/945; 148/100, DIG. 24, 900, DIG. 51; 427/127, 129, 130

[56] References Cited

U.S. PATENT DOCUMENTS

| | | | |
|---|---|---|---|
| 3,759,745 | 9/1973 | Dixon et al. | 117/237 |
| 3,838,450 | 9/1974 | Bongers et al. | 252/62.57 |
| 3,989,352 | 11/1976 | Lacklison et al. | 350/151 |
| 4,451,500 | 5/1984 | Gerard et al. | 427/38 |
| 4,497,545 | 2/1985 | Noss | 350/376 |
| 4,500,176 | 2/1985 | MacNeal | 350/376 |
| 4,500,177 | 2/1985 | MacNeal | 350/376 |
| 4,544,239 | 10/1985 | Shone et al. | 350/376 |
| 4,604,577 | 8/1986 | Matsumura et al. | 324/244 |
| 4,608,142 | 8/1986 | Gomi et al. | 204/192 M |
| 4,625,167 | 11/1986 | Fitzpatrick | 324/235 |
| 4,625,390 | 12/1986 | Shone et al. | 252/62.57 |
| 4,711,694 | 12/1987 | Capra et al. | 156/603 |
| 4,728,178 | 3/1988 | Gualtieri et al. | 350/377 |
| 4,755,752 | 7/1988 | Fitzpatrick | 324/228 |

OTHER PUBLICATIONS

NERAC Reports 487-498, Nov. 22, 1990.
NERAC Report 13, Nov. 26, 1990.

Primary Examiner—Paul J. Thibodeau
Assistant Examiner—R. Follett
Attorney, Agent, or Firm—Michael H. Wallach

[57] ABSTRACT

A bistable single crystal magneto-optic film of preselected coercivity is described. The film is readily switchable and is characterized by a substantially square shaped hysteresis loop. The film properties are attributed to controlled introduction in the film of defects of predetermined size and distribution. Defects of from about 0.4 μm to about 4.0 μm present in numbers per cm$^2$ of from about 10 to about 10$^6$, with optimal distribution falling in the range of from about 100 to about 1000, are described. Also described are methods of achieving the required defect size and distribution utilizing procedures such as ion bombardment, particle abrasion/deposition, laser ablation or annealing of the film or substrate upon which the film is supported. Devices in which the films can be used to advantage, such as flaw detecting, imaging and microwave processing, are described.

36 Claims, 10 Drawing Sheets

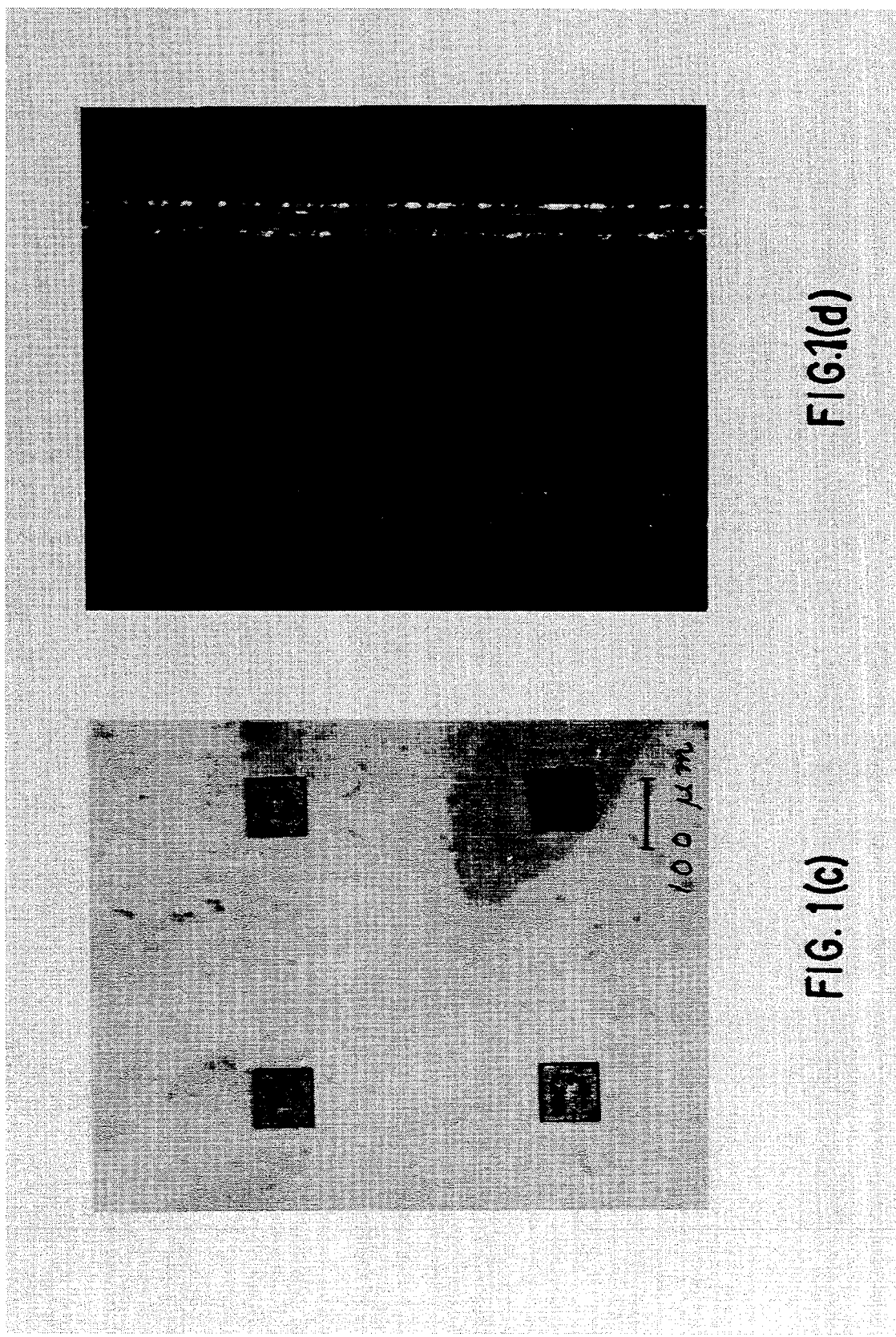

BISTABLE MAGNETO-OPTIC SINGLE CRYSTAL FILMS AND METHOD OF PRODUCING SAME UTILIZING CONTROLLED DEFECT INTRODUCTION

BACKGROUND OF THE INVENTION

1. Field of the Invention

The present invention relates to magneto-optic films, methods of preparing same and devices incorporating such films.

2. Description of the Prior Art

Magneto-optic films and/or various devices utilizing same have been described in the following patents, the teaching of which is incorporated herein by reference thereto: U.S. Pat. Nos. 4,500,173 and 4,500,177, directed to spatial light modulators. U.S. Pat. Nos. 4,625,167 and 4,755,752, directed to crack detection devices; U.S. Pat. No. 4,728,178, directed to switches, modulators; U.S. Pat. No. 4,604,577, directed to magnetic field sensors; and, U.S. Pat. Nos. 3,838,450; 3,989,352 and 4,608,742, directed to memory and recording/modulator devices. Magneto-optic films have also been used in optical isolators, see e.g., *Fujitsu Science & Tech. Journal*, Vo. 26, No. 26. Such films may also find utility in rotation sensors for brakes.

One of the drawbacks of monocrystalline ferrimagnetic oxide films has been the low coercivity (less than 1 Oe) of such films. See, e.g., Hansen et al. "Media for Erasable Magneto-optic Recording" *IEEff Trans. Mag.*, Volume 25, pp. 4390–4404. . As an alternative to the low coercivity monocrystalline ferrimagnetic films the art has produced ferrimagnetic polycrystalline films. Such magneto-opt films have been prepared utilizing sputtering, vapor deposition or spray pyrolysis. However, such polycrystalline films have coercivity values of 200–2,000 Oe. These values are too high for the applications which the films of the present invention find utility, because of the high switch fields required.

The herein invention resides in the discovery that monocrystalline ferrimagnetic oxide films having good square shaped hysteresis loops of predetermined coercivity can be produced by imparting to such films defects of controlled size, number, and distribution. The present invention enables replicable production of monocrystalline ferrimagnetic oxide films which operate at low switch fields, The present invention now allows retention of the desirable properties of monocrystalline ferrimagnetic oxide films while modifying the low coercivity levels characteristic to such materials and providing a readily switchable film having a good square shaped hysteresis loop.

SUMMARY OF THE INVENTION

In accordance with the present invention, bistable magneto-optic films of predetermined switching field are produced by introducing defects (1) within and/or (2) on the surface of such films and/or (3) at the interface of such films with substrates. The predetermined switching field is achieved by controlling size, number, and distribution of the defects imposed.

One aspect of the present invention relates to a bistable single crystal magneto-optic film of preselected coercivity having induced defects distributed therein, the size of said defects being from about 0.4 $\mu$m to about 4.0 $\mu$m and the number of said defects per cm$^2$ being within the range of from about 10 to about 10$^6$. The preferred defect size is from about 0.6 $\mu$m to about 2.0 $\mu$m and the preferred number of defects per cm$^2$ is within the range of from about 10$^2$ to about 10$^4$. The most preferred defect size is from about 0.8 $\mu$m to about 1.2 $\mu$m and the most preferred number of defects per cm$^2$ is within the range of from about 100 to about 1,000. Preferably the preselected coercivity falls in the range from about 1 Oe to about 50 Oe, most preferably, less than about 10 Oe. The bistable single crystal magneto-optic films of the present invention most preferably have a coercivity of from about 1 to about 10 Oe, anisotropy field of from about 1,000 to about 6,000 G, switch field from about 1 to about 10 Oe and a saturation magnetization that is from about 100 to about 150 gauss.

Another aspect of the invention involves improvements in certain devices associated with the substitution of the film of the present invention for the prior art magneto-optic films used in such devices.

Thus, another aspect of the invention relates to a pixel array comprising a subdivided single crystal magneto-optic film wherein the improvement of the present invention comprises utilizing the heretofor described bistable single crystal magneto-optic film of preselected coercivity having induced defects distributed therein, the size of said defects being from about 0.4 $\mu$m to about 4.0 $\mu$m and the number of said defects per cm$^2$ being within the range of from about 10 to about 10$^6$. In the preferred pixel array, the defect size is from about 0.6 $\mu$m to about 2.0 $\mu$m and the number defects per cm$^2$ is within the range of from about 10$^2$ to about 10$^4$. In the most preferred pixel array, the coercivity is in the range of from about 1 Oe to about 10 Oe and the defect size is from about 0.8 $\mu$m to about 1.2 $\mu$m and the number of defects per cm$^2$ is within the range of from about 100 to about 1000.

Yet another aspect of the present invention relates to an apparatus for detecting and providing images of flaws, voids, discontinuities, or the like in a target material by observing magnetic field perturbations in a magnetic material wherein the improvement of the present invention comprises utilizing as said magnetic material a bistable single crystal magneto-optic film of preselected coercivity having induced defects distributed therein, the size of said defects being from about 0.4 $\mu$m to about 4.0 $\mu$m and the number of said defects per cm$^2$ being within the range of from about 10 to about 10$^6$. In the preferred flaw detecting and imaging apparatus, the defect size is from about 0.6 $\mu$m to about 2.0 $\mu$m and the number of defects per cm$^2$ is within the range of from about 10$^2$ to about 10$^4$. In the highly preferred flaw detecting and imaging apparatus, the coercivity is in the range of from about 1 Oe to about 10 Oe and the defect size is from about 0.8 $\mu$m to about 1.2 $\mu$m and the number of defects per cm$^2$ is within the range of from about 100 to about 1,000. In the most highly preferred flaw detecting and imaging device, the coercivity is in the range of from about 2 Oe to about 6 Oe, and the magneto-optic film has a saturation magnetization of from about 100 gauss to about 150 gauss and an anisotropy field of from about 1,000 to about 6,000 G. The film thickness of the flaw detecting and imaging apparatus of the present invention is most preferably from about 2 to about 3.5 $\mu$m.

Yet a further aspect of the present invention relates to a microwave signal processing unit including a Fresnel or Fourier transformer comprised of a pixel array of independently switchable pixels of magneto-optic film. The improvement of the present invention comprises utilizing, as said pixel array, a subdivided bistable single crystal magneto-optic film of preselected coercivity having induced defects distributed therein, the size of said defects being from about 0.4 μm to about 4.0 μm and the number of said defects per cm$^2$ being within the range of from about 10 to about 10$^6$. Preferably the magneto-optic film has a coercivity in the range of from about 1 Oe to about 50 Oe, the size of the defects in said film is from about 0.8 μm to about 1.2 μm and the number of said defects per square centimeter is within the range of from about 100 to about 1,000. Most preferably the bistable single crystal magneto-optic film has a coercivity less than about 10 Oe. Additional highly preferred characteristics of the bistable single crystal magneto-optic film are a coercivity of from about 1 to about 10 Oe, an anisotropy of from about 1,000 to about 6,000 G, a switch field of from about 1 to about 10 Oe and a saturation magnetization of from about 100 to about [50 gauss.

Yet another aspect of the present invention relates to a magneto-optic light deflector. The improvement of the present invention comprises utilizing as the magneto-optic element for such device, a bistable single crystal magneto-optic film of coercivity in the range of from about 1 Oe to about 50 Oe having induced defects distributed therein, the size of said defects being from about 0.8 μm to about 1.2 μm and the number of said defects per square centimeter being within the range of from about 100 to about 1,000. Preferably the film coercivity is less than about 10 Oe. Most preferably the coercivity is from about I to abut 10 Oe, the anisotropy is from about 1,000 to about 6,000 G, the switch field is from about 1 to about 10 Oe and the saturation magnetization is from about 100 to about 150 gauss.

Part and parcel of the present invention are the alternative processes developed to achieve the defect architecture which provides the properties of the films of the present invention. Accordingly, in the manufacture of a magneto-optic monocrystalline film the present invention includes the improvement comprising inducing defects in said film of size within the range of from about 0.4 μm to about 4.0 μm and distribution within the range of from about 10 to about 10$^6$ per cm$^2$ to form a bistable magneto-optic film of preselected coercivity in the range of from about 2 to about 50 Oe. In accordance with the preferred improved method of manufacture of the present invention, the defect size is from about 0.6 μm to about 2.0 μm and the number of defects per cm$^2$ is within the range of from about 10$^2$ to about 10$^4$. In accordance with the most preferred method of manufacture of the present invention, the defect size is from about 0.8 μm to about 1.2 μm and the number of defects per cm$^2$ is within the range of from about 100 to about 1,000.

Defects in the monocrystalline film may be induced by mechanical abrasion of a substrate supporting the film followed by formation of monocrystalline film on the abraded surface of said substrate. At the loci of substrate defects, when the film is grown, defects are propagated in the film. Defects in the film may be directly induced by mechanical abrasion of the exposed surface of the monocrystalline film.

Defects in the film may also be induced by particle deposition on the surface of a substrate supporting the film. The substrate surface is then heated to cause decomposition or diffusion of particles on the substrate surface thereby forming defects on and/or in the substrate extending downwardly from the surface. When the monocrystalline film is formed on the surface of the substrate, the substrate defects are replicated/carried over into the film. Defects in the film may additionally be induced by particle deposition on the exposed surface of the monocrystalline film after its formation (suitably by liquid phase epitaxy) on a monocrystalline garnet substrate. The exposed surface of the film is heated to cause decomposition or diffusion of the particles on/into the film surface.

Defects in the film also may be induced by heavy ion impingement of the substrate followed by deposition of an epitaxial monocrystalline film on the abraded surface of such substrate. Defects in the film may also be induced by the previously described heavy ion impingement of substrate followed by chemical etching to increase the size of defects which are formed by the heavy ion impingement. The film of the present invention is formed on the abraded and etched surface of the substrate.

The defects in the film may also be induced by heavy ion impingement without the added step of etching. Defects in the film may also be induced by laser ablation of the substrate followed by formation of epitaxial film on the abraded surface of the substrate or directly by laser ablation of the exposed surface of the film.

Depending on the particular application for the film, the size and distribution of the defects can vary, with the defect size varying from about 0.4 to about 4.0 μm and the number of defects per cm$^2$ falling in the range of from about 10 to about 10$^6$. Preferably the defect size is from about 0.6 to about 2.0 μm with the number of such defects per square centimeter being within the range of from about 10$^2$ to about 10$^4$. The most preferred defect size is from about 0.8 to about 1.2 μm with the number of such defects per square centimeter being within the range of from about 100 to 1,000. Defect size, as used herein, signifies the maximum extent of a hole, inclusion, or other artifact which has no magnetic properties equal to the adjacent areas of the film.

The defect configuration is highly dependent on the method of defect generation. In the case of laser ablation, the defect can be defined by reference to width and depth of the ablated hole, which, when viewed by electron microscopy, appears as a right circular cylinder, Of course, the defect configuration in laser ablation can be control led, as is appreciated in the art, by selecting beam properties determined by the optical system of the laser ablater. In the case of defects formed by annealing, it is believed the defect is formed by nucleation of a second phase, within the film, which resulting phase and accompanying strain field, when observed by optical methods, roughly approximates a sphere and, when observed by electron microscopy, appears as a truncated ellipsoid.

Mechanically induced defects in the substrate, when observed optically after etching, appear as triangular based pyramidal pits with the base in the plane of the film/substrate surface; the size of defect being measured by reference to maximum width of the triangular base. Defects produced by ion implantation have the same triangular configuration observed where defects are mechanically induced.

In the case of mechanically induced defects by particles/ions, defect size refers to the maximum width of the triangular pit which is formed. In the case of defects generated by annealing, defect size is taken as the diameter of the optically observed defect; and, in the case of laser ablated defects, defect size is determined by reference to the diameter of the ablated hole at the surface of the film/substrate.

Depending on the operational requirements of the film, a few defects above about 10 μm may be tolerated, though not necessarily with the same results achieved within the preferred size range; however, the defect size should be within the range of from about 0.4 to about 4 μm and the number of defects per square centimeter should be from about 100 to about $10^6$ in order to achieve film properties of the type and order required for bistable magneto-optic films of the present invention. The domain wall width determines the size of the defect to be tolerated. If $_{w1}{\cong}0.4$ μm, $^{w1}$ defects of less than this can be tolerated. Defects larger than this will affect coercivity. Those at 0.3–4 μm are helpful. Larger ones may not be tolerable.

In order to achieve defects of required size and distribution it is important that the substrate be substantially free of defects. This means that defects in the range of from about 1 to about 5 μm should preferably be less than about $5/cm^2$ and most preferably no more than $2/cm^2$ as determined by microscopic observation to a resolution of ±0.5 μm. Defects above 5 μm in the substrate prior to controlled defect formation degrade the performance of the films finally produced in accordance with the present invention and the starting substrate and/or film deposited thereon preferably is free or substantially free of such defects. Films wherein defects above 5 μm are present at levels greater than $0.5/cm^2$, though operative, display unacceptable background clutter believed to be caused by such defects permanently pinning moving domain walls.

Distribution of the Defects

To achieve optimal effect the defects should be substantially evenly distributed; that is, locations where the defect density is too high or too low should be avoided. Significant numbers of such areas can adversely affect operation of the film.

Where the defect density (number of defects per $cm^2$) is too high there is a loss of bistable domain structure with attendant loss of contrast.

Where the defect density is too low then there are not enough sites for domain wall generation and switching does not occur.

In the preferred universe of magneto-optic films 100–1,000 defects/$cm^2$ provide the low switching fields required in films and devices incorporating same in accordance with the present invention.

It has been observed that if defects are clustered in close proximity and the size of the cluster exceeds the maximum operable particle size, this causes permanently pinned domains which manifest themselves as noise in the viewing with loss of resolution and contrast in the region of the defect cluster.

One of the attendant advantages of the present invention where coercivity levels in optimal operating ranges are achieved by defect introduction is the observed square hysteresis loop at low switching values, Thus, for example, at the typical low switching fields of 1 to 10 Gauss, the stability of the domain structure and sharpness of the image are enhanced with the squareness of the hysteresis loop.

The film and substrate combinations suitable for use in the present invention may be substantially lattice matched or in compression or tension. Where the film is in compression, up to about 0.03 angstroms compression is suitable. Where the film is in tension, then up to 0.01 angstroms tension is suitable. Among the films suitable for use in the present invention prior to introduction of defects, are films of the type described in U.S. Pat. No. 4,625,390, the teaching of which is incorporated herein by reference thereto.

Where the magneto-optic film is to be used in defect detection, devices of the type described in U.S. Pat. Nos. 4,625,167 and 4,755,752, the preimposed defect-free film, that is, the film in the absence of defects most preferably has the following properties:

1. a saturation magnetization of 100–150 gauss;
2. a switching field of about 100 Oe up to about 150 Oe;
3. magnetic anisotropy of 2,000–6,000 gauss;
4. and a coercivity of less than about ½ gauss.

Although not necessarily with same effect, the film prior to defect introduction can have saturation magnetization extending from 50 to 300 gauss (preferably 50–200); a switching field of up to 200 Oe; a magnetic anisotropy of about 2,000 to about 10,000 with 8,000 or less gauss being the preferred upper limit; and a coercivity less than about 5, preferably around 1 or less down to about 0.5.

After modification of the foregoing films in accordance with the present invention, to produce the imposed defect, low switching field films of the present invention the film properties are as follows:

1. Saturation magnetization, 100–150 gauss.
2. Switch field of 1–10 Oe.
3. Anisotropy of 1,000–6,000 G.

Coercivity of 1–10 Oe.

The only noticeable change in accordance with the treatment of the present invention is in coercivity and switching field. Accordingly, in developing the requisite film characteristics for various applications for which the bistable magneto-optic single crystal films of the present invention are used, the starting material can be selected without regard to compensation for defect introduction; that is, introduction of defects in accordance with the present invention can be used to manage coercivity without adversely effecting other film properties. For most applications coercivity values of from about 2 to about 50 Oe would be targeted with levels of 10 Oe being typical at the high end. For devices such as crack detection devices the films used preferably have a coercivity of from about 2 to about 6.

For other devices besides crack detection, other properties such as magnetization, anisotropy, Curie Point, domain type, would also have to change. Other means may be necessary to generate or detect switched areas.

The methods of imparting the defects to the substrate and/or film surface are numerous and include:

a. the use of diamond powder, suitably 1 μm in diameter which is blown against substrate or film to form defects where the diamond particles impact;

b. the use of particles such as latex (C), dust ($SiO_2$) or polishing agent ($Al_2O_3$) by depositing same on the surface of substrate and/or film and then heating the surface to cause decomposition and/or diffusion to form the defects; latex spheres, dust or bacteria of 0.01 to 1.0 μm size when deposited on substantially defect-free GGG substrate, followed by heating of the GGG to 700° C., react with the GGG to form defects in the GGG which are replicated in the film when grown c. the use of heavy ions (Z>30) which are accelerated and impinged on the surface, optionally followed by chemical etching to increase defect size; and the use of ions of H+, He$^{2+}(\alpha)$ and Au+ at energies of 6 Mev and doses of $10^{12}$–$10^{15}$ ions/cm$^2$ can be used. Where the lighter ions of H+ or He$^{2+}$ are used the bombarded surface is etched to increase defect size. Au, which is preferable to the lighter ions, introduces damage sites of larger size than the lighter ions which can also be increased by etching.

d. the use of excimer lasing;

in this procedure excimer lasers 192, 248 or 308 nm are suitably employed to ablate material in a substrate or a magnetic film; the laser beam size can be control led over an area of 1–10$^4$ $\mu$m$^2$, the pulse cherry is suitably from 1–300 and the pulse repetition rate may be from 1–200 Hz; the substrate or film, the number, size, depth and distribution can be control led for the defects by controlling energy, beam optics and mechanical movement of the sample.

BRIEF DESCRIPTION OF THE DRAWINGS

FIG. 1(c) is a photomicrograph of a rectangular array of 100 $\mu$m ablations on 500 $\mu$m centers.

FIG. 1(d) is a photomicrograph of continuous lines of 2–6 $\mu$m width drawn on GGG.

(a) arbitrary sample direction with field increased to 60 Oe (b) sample rotated by 180°

(c) field increased to +60 Oe reduced to +20 and swept to −23 Oe (d) loop with symmetric slow transition at −5 Oe.

Figure 4A:

FIG. 4(a) is a secondary electron micrograph illustrating an ablated hole (defect) formed with a 248 mn excimer laser pulse at a fluence of 10 J/cm$^2$, 10 pulses at 100 Hz.

Figure 4B:

FIG. 4(b) is an optical micrograph of a triangular in the film generated by 3micron diamond abrasion of the substrate prior to growth.

Figure 4C:
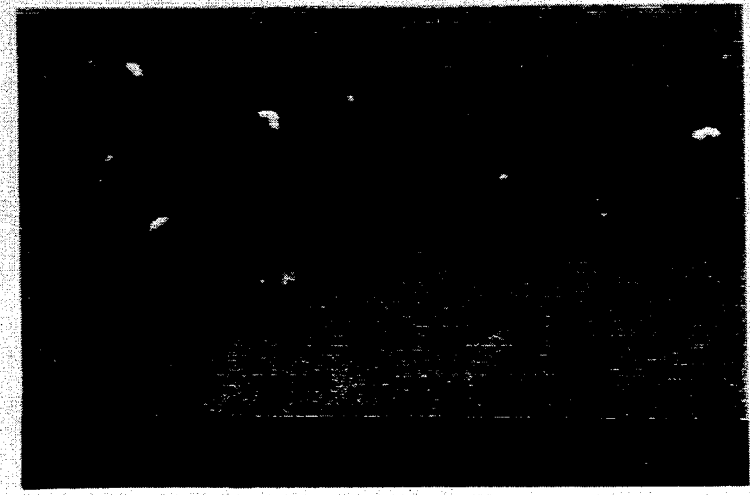

FIG. 4(c) is a secondary electron micrograph of a defect in the bulk of the film generated by annealing the film in oxygen for 53 minutes at 1050° C.

Figure 5:
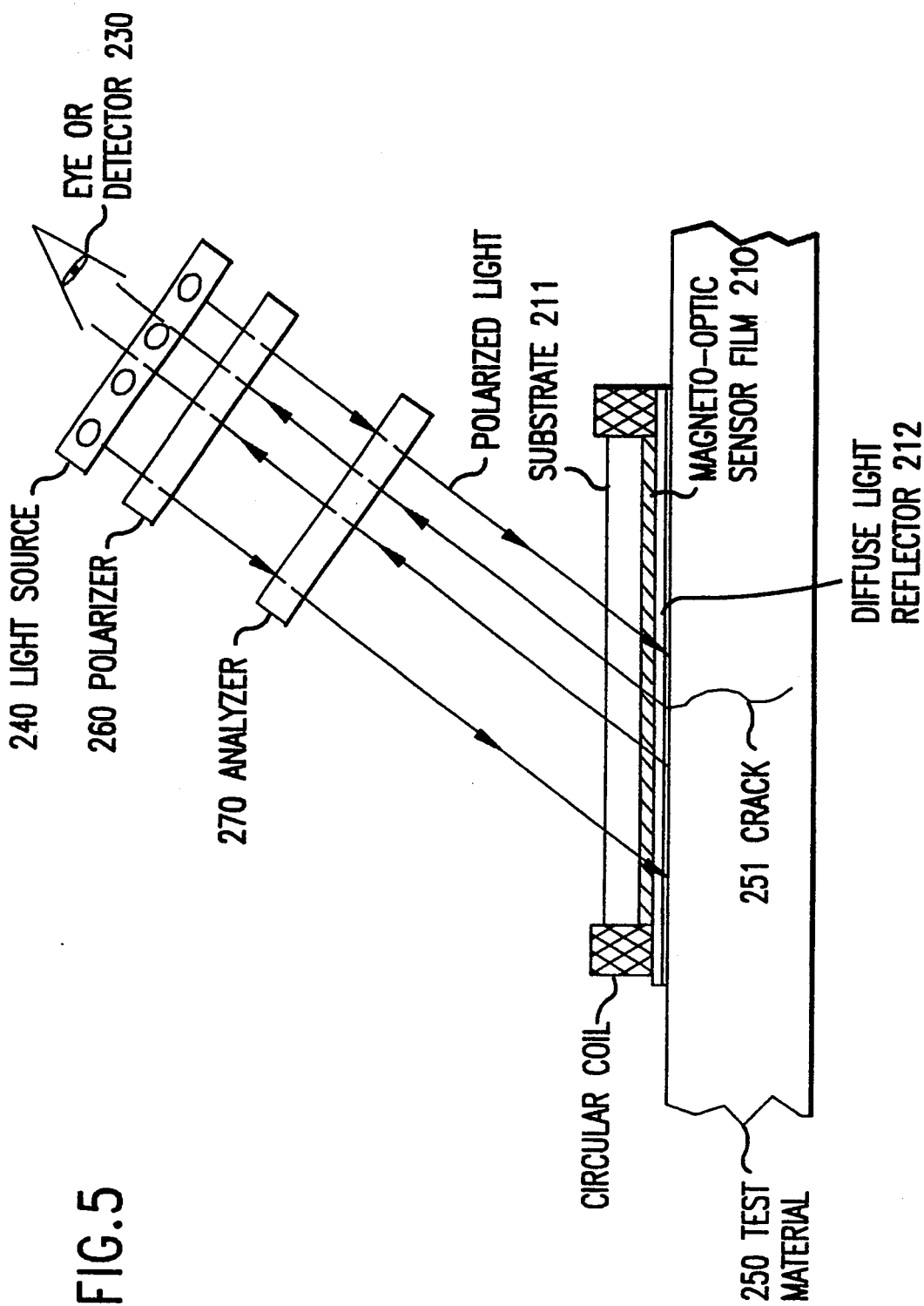

FIG. 5 is a schematic representation of a crack detecting device illustrating the device's sensing head comprised of a magneto-optic film covered with a reflector (100 micron thick metallic layer) placed over a test sample with crack shown.

Figure 6:
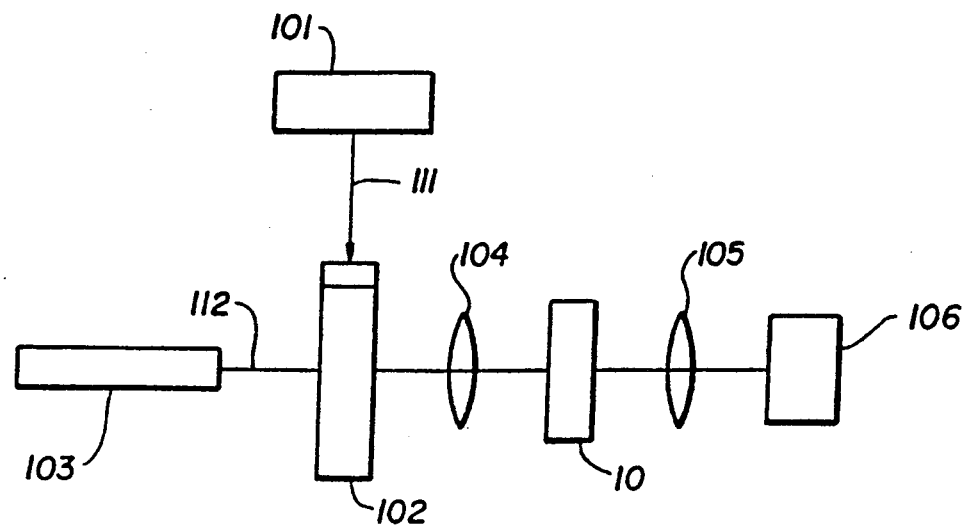

FIG. 6 is a simplified side view of a signal processing device.

Figure 7:
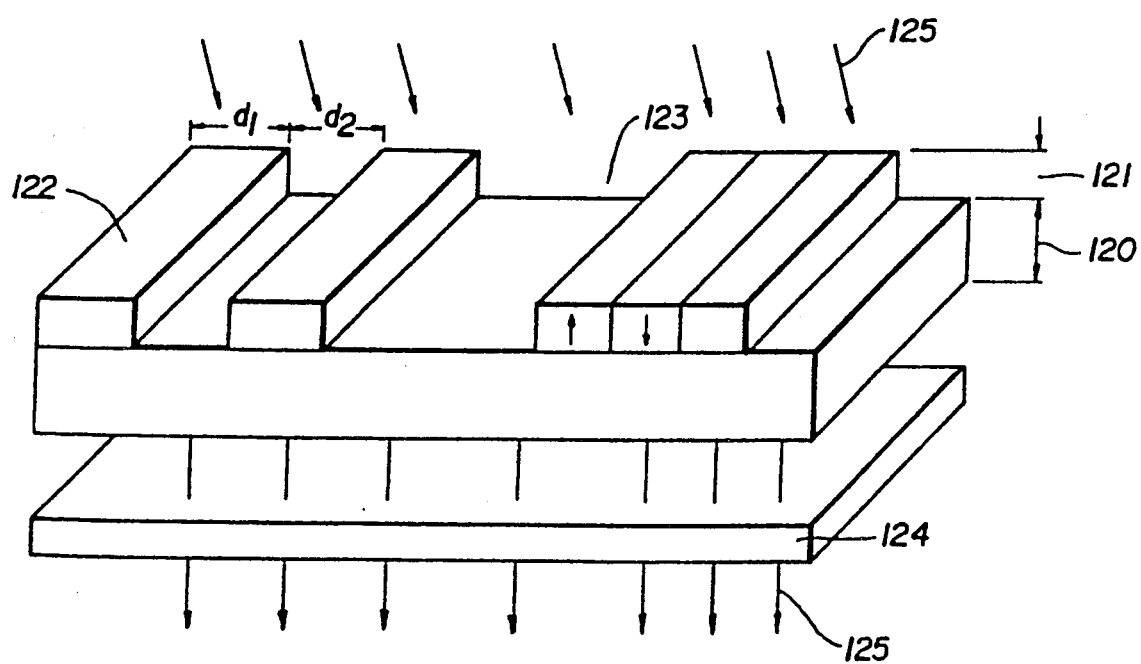

FIG. 7 is a simplified perspective view of a magneto-optic light deflector.

Figure 8:
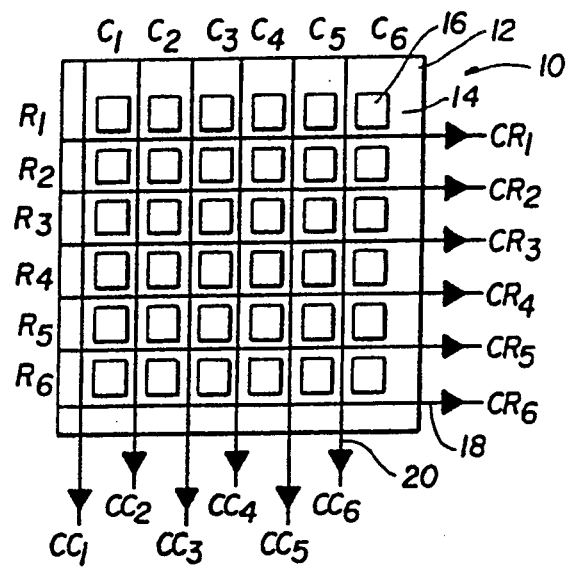

FIG. 8 is a simplified view of a conventional magneto-optic chip showing the rows and columns of the posts thereon as well as the matrix of control wires connected to provide individual addressibility of the posts which form the pixel positions.

Figure 9:
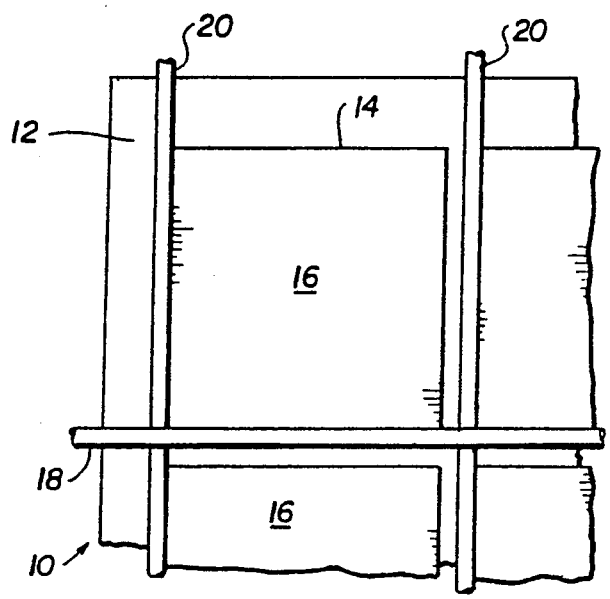

FIG. 9 is an enlarged drawing of a single post area on the chip of FIG. 8.

Figure 10:
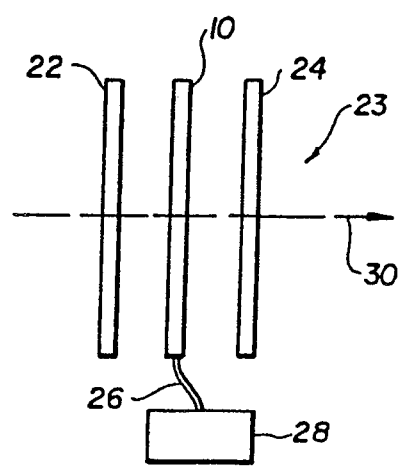

FIG. 10 is a simplified side view of a display chip showing its conventional mode of operation.

Figure 11:
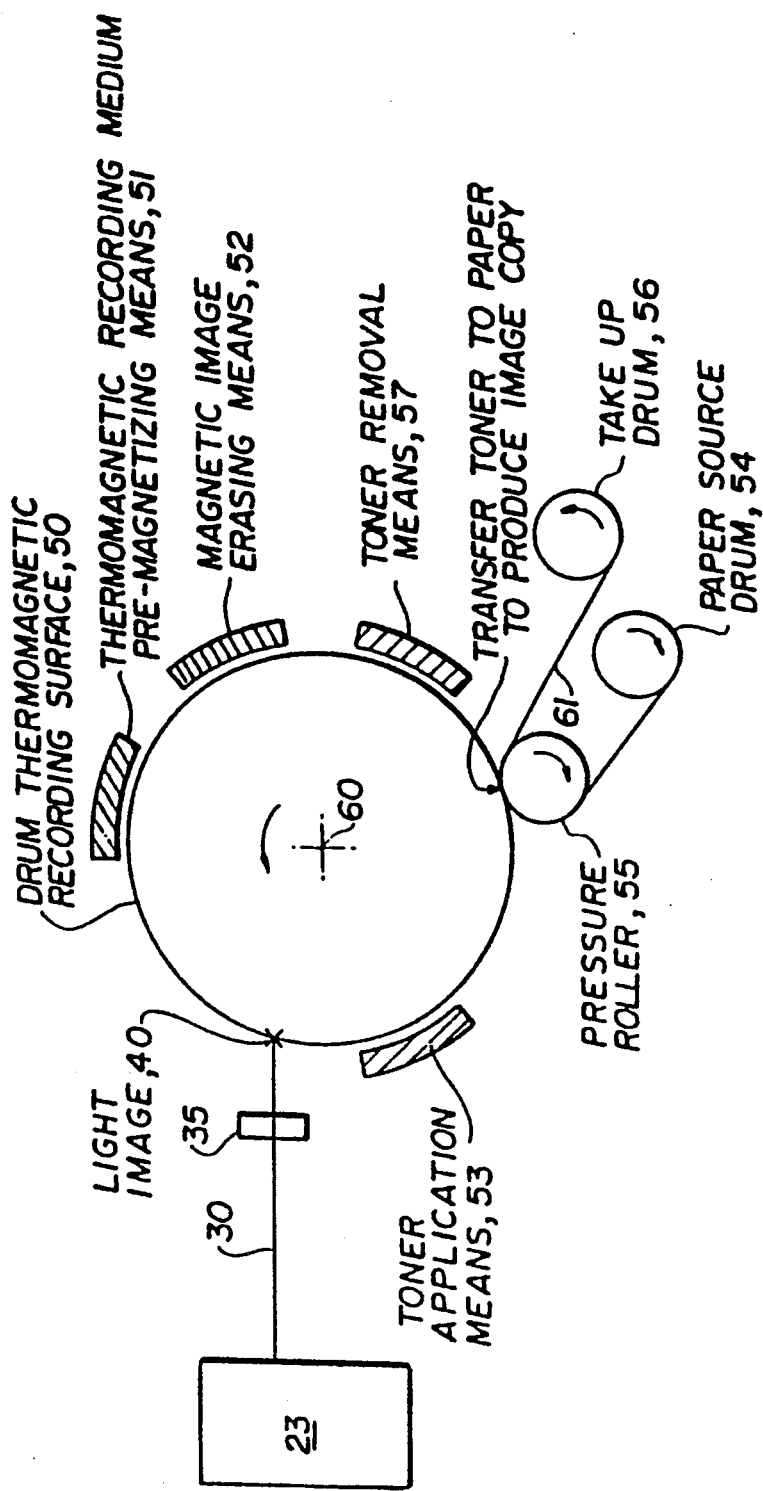

FIG. 11 is a pictorial diagram of a recording device employing a thermomagnetic recording system.

DETAILED DESCRIPTION OF THE INVENTION

The present invention derives from an investigation directed to the development of a magnetic film of suitable switching field, namely, 2–4 G, for eddy current-crack detection imaging. In development of our switchable film, we started by selecting a film composition that would fit the commercially available substrate of GGG (Gd$_3$Ga$_5$O$_{12}$). Attendant magnetic properties required were estimated. The composition and properties of the film selected are listed below in Table I.

TABLE I

| Typical Film Properties | |
|---|---|
| Film Composition: | Bi$_1$Tm$_2$Fe$_{3.1}$Ga$_{1.9}$O$_{12}$ |
| Substrate: | (111) oriented Gd$_3$Ga$_5$O$_{12}$ |
| Index of refraction: | 2.35 at 633 nm |
| Saturation magnetization: | 100–150 G |
| Optical absorption: | $\alpha = 1000$ cm$^{-1}$ at 546 nm |
| Magnetic anisotropy: | 2000–6000 G |
| Faraday rotation: | at 546 nm 2.3°/$\mu$m |
| Switching field: | 2–4 G |
| Curie temperature: | 80° C. |
| Film lattice mismatch to substrate: | 0.000–0.005 Å in compression |
| Thickness: | 2.0–3.5 $\mu$m |
| Thickness uniformity: | ±0.2 $\mu$m |

The values of the below enumerated magnetic and physical properties were selected based upon our reasoning set forth below.

1. Film Thickness

We reasoned a film thickness of 2.0–3.5 $\mu$m would be ideal. A film thicker than 3.5 microns would be too dark to see through due to the optical absorption of the iron in the films—such iron being necessary to make the film magnetic. Below 2 $\mu$m the Faraday rotation for the optical imaging of the device would be too low to give adequate contrast.

2. Stable Magnetic State

We reasoned that the film must be magnetically bi-stable in order to work in the device. By hi-stable we mean the film must consist of ideally one single magnetic domain or several large cm$^2$ sized domains which will stay magnetized in either the up or down magnetic state in the absence of an applied magnetic field. Magnetic film can exist ideally in two types of magnetic domain states. The first is the hi-stable state and the other is the serpentine state, In the latter magnetic domain state the magnetic domains are broken up into equal numbers of up and down magnetic domains in the absence of an applied magnetic field. These domains are typically in the shape of long, thin serpentine areas. Hence the etymology of the descriptive name serpentine domains. The width of these domains is typically 10–30 $\mu$m wide. Factors such as saturation magnetization, magnetic anisotropy, and thickness of the film, determine which magnetic state is stable. The film composition selected, $Bi_1Tm_2Fe_{3.1}Ga_{1.9}O_{12}$, produces a hi-stable magnetic domain below about 4 μm in thickness and a serpentine domain structure above 4 μm. This film composition met the bi-stable magnetic domain requirement, the thickness requirement and the commercially significant criteria of having a lattice constant appropriate for commercially available GGG ($Gd_3Ga_5O_{12}$) substrate.

3. Low Switching Field

This property was one imposed by the requirements of current crack detection devices. For the film to work in such devices for eddy current crack detection, a low switching field would be required. In operation such devices induce the flow of an eddy current through any metallic material. When the eddy current passes around a rivet hole or crack the current forms a current loop which generates a small magnetic field. For the device to work, this field must alter the magnetic state of the magneto-optic film. A 150–200 ampere eddy current only generates a very small (circa 2 gauss field) at crack locations. The film must therefore also have a low switching field of about 2 gauss in order for the 2 gauss magnetic field caused by the eddy current generated at a crack to switch the magnetic state of the film at the locus of the crack in the metallic material (e.g., a plane skin crack).

The switching field of the film is governed by the method of magnetic switching. In a film of serpentine domain structure, the switching occurs by the movement of existing domain walls. This switching field is in the order of the coercivity field, which is the field required to start the motion of a perfect defect-free domain wall. For nearly perfect films this field is quite low, often only 0.5 G or less. For hi-stable, single domain films, switching probably occurs by coherent rotation. The field required to switch such films is in the order of the magnetic anisotropy field which is thousands of gauss. The switching field is high because a domain wall must be generated by the applied field to initiate switching. This is quite different for the low field required of a serpentine domain structure where the domain wall already exists and only has to be moved to accomplish switching. We reasoned that since a bi-stable magnetic domain and low switching field are both required, the switching field must be lowered by some method. We further reasoned that the switching field could be lowered by the introduction of stress into the films to lower the stress-induced component of the magnetic anisotropy and/or by the introduction of defects into the film. The defects would locally, on a micron scale, lower the switching field from thousands of gauss to several gauss.

Based on this reasoning a series of films were grown with varying amounts of compressive stress in them to alter the stress induced anisotropy. The film properties are tabulated below in Table II.

TABLE II

| Film Grown With Stress Variation | | | | |
|---|---|---|---|---|
| Film ID | Switching field (G) | Thickness (μm) | Film lattice mismatch to substrate - Å | Defect density defect/cm$^2$ |
| BB-70 | 2.2 | 3.2 | 0.000 | 3.8 |
| BB-77 | 2.3 | 3.1 | 0.000 | 29.8 |
| BB-82 | 2.3 | 2.7 | 0.001T | 10.3 |
| BB-85 | 2.3 | 2.6 | 0.004C | 25.5 |

TABLE II-continued

| Film Grown With Stress Variation | | | | |
|---|---|---|---|---|
| Film ID | Switching field (G) | Thickness (μm) | Film lattice mismatch to substrate - Å | Defect density defect/cm$^2$ |
| BB-87 | 2.0 | 3.0 | 0.014C | 65.0 |

T = tension
C = compression

The film lattice mismatch to the substrate is a measure of residual stress in the film generated by an intentional mismatch in lattice constant between the film and substrate. The larger the mismatch the greater the stress with T meaning in tension and C meaning in compression. The film thickness is in microns and the switching field is measured in Gauss.

Upon examination of these films in an eddy current-crack detection device of the type described in U.S. Pat. Nos. 4,625,167 and 4,755,752, we discovered that the BB-70 and BB-82 films behaved radically different from the rest of the films. These two films exhibited large areas that would not switch magnetically in the crack detection device. Films BB-77, BB-85 and BB-87 exhibited a much more uniform image and for the most part could be magnetically switched. At first this behavior was attributed to the degree of stress in the films. As mentioned earlier, this reduction in the stress component of the magnetic anisotropy can lower the switching field. At this point in time the defect density of the films had not yet been measured.

The defect density was measured as an afterthought and the variation in defect density among films was a random occurrence related to the specifics of the film growth technique used. In particular, defect density was related to the cleaning method used for preparing the substrates for epitaxial growth.

Films were cleaned by a home made oxygen plasma cleaner. The films were mounted in a Pt growth holder and pre-cleaned with an 80° C. ionic laboratory detergent solution rinsed in hot deionized water. After drip drying in front of a HEPA filter, the substrate holder was placed in the vacuum chamber of the oxygen plasma cleaner. The chamber was pumped out to $10^{-3}$ torr and a small flow of 0.2 μm filtered oxygen gas was introduced into the chamber. At this point the chamber was exposed to the microwave radiation from an ordinary household microwave oven causing the oxygen gas inside the chamber to ionize into oxygen radicals. The substrate is exposed to six minutes of this oxygen plasma before venting the chamber and removing the substrate for subsequent film growth. The exposure of the substrate to the oxygen radicals, strips the last traces of organic contamination off of the substrate surfaces leaving the substrate very clean. The extent to which the substrate was cleaned is checked after the film has been grown. Each speck of contamination on the substrate prior to growth shows up as a magnetic domain pinning defect after the film is grown. These defects are counted in an optical microscope. Since many of the defects are submicron in size and below the detection limits of the optical microscope, they are detected by observing the motion of the magnetic domains generated in the magneto-optic film when exposed to a circa 30 hz A.C. magnetic field. The actual film defects are located at the sites where the magnetic domains are pinned. The film defect density is determined by counting the number of defects observed over a known area of film.

We next prepared a series of films grown using improved growth methods to ensure the highest quality and also to achieve a low defect density thereby minimizing what we apprehended to be the detrimental effect of the defects.

TABLE III

Films With Low Defect Densities

| Film ID | Switching field | Thickness (μm) | Film lattice mismatch to substrate - Å | Defect density defect/cm² |
|---------|-----------------|----------------|----------------------------------------|---------------------------|
| BB-104  | 2.8             | 3.0            | 0.006 (C)                              | 0.2                       |
| BB-105  | 3.0             | 3.0            | 0.005 (C)                              | 3.7                       |
| BB-107  | 2.0             | 3.0            | 0.005 (C)                              | 0.3                       |
| BB-109  | 2.1             | 3.0            | 0.006 (C)                              | 0.1                       |
| BB-111  | 2.0             | 3.0            | 0.004 (C)                              | 0.1                       |

As can be seen, the switching field, thickness, and lattice mismatch were all in the range that should have resulted in workable films, yet when tested in an eddy current crack detection device, none of the films would switch at all. The results observed suggested that defects were necessary in the operation of the device in which the magneto-optic film is erased by a switch field pulse 30 times a second.

Although not wishing to be bound it is believed that the role of defects which we discovered are two fold. First, in order to nucleate a domain wall at a low field, it is believed that defects must exist in the film to locally lower the magnetic anisotropy. The fact that static switching shows a low switching field is because only a small number of defects are required in a 3 inch diameter film to initiate switching. Some native defects are always grown-in and distributed throughout a "perfect" film, particularly at the rounded or ground film edges. Domains are nucleated at these regions in very low fields. Since the applied field is slowly increased over several seconds only a small number of domain walls need to be nucleated in order to eventually switch the entire 3 inch film. At a 30 Hz operation rate domain walls must be nucleated in many spots because the domain wall can only travel a short distance before it encounters a reverse magnetic field and must change its direction of travel. This, it is believed, explains why films grown under less than ideal conditions (defect density (d) =circa 30–60d/cm²) would work in the crack detection device but a clearly superior, higher quality film with lower defects would not work.

After our observations of the unexpected results obtained using the low defect density films of Table III, development work was commenced to find ways to introduce defects of known size and distribution into the film. As a result of this work it was found that defects below a certain size do not influence the domain wall motion; and, that defects above a certain size permanently pin or impede the motion of a domain wall. The pinned domain wall manifests itself as snake-like streaks in the image generated by films incorporated in crack detection devices. Such images interfere with contrast and resolution of images generated by very small cracks. Moreover, it was also observed that the location of the defect affects the operable size range of the required defects. A defect on the surface of the film must be much larger, circa 4 μm, to nucleate the domain wall as contrasted with a defect generated in the bulk of the film. This latter defect can be about 1 μm to produce the same effect as a film surface defect of 4 μm.

It was also observed during development of the film that the distribution of defects was critical to achieving acceptable film performance.

In a process that randomly generates defects in a film, regions exist where several defects will occur close together (clustering). Such regions have an effective size greater than the size of each individual defects. If this region size is of a size that will permanently pin the magnetic domains, the snake-like defects already mentioned occur. These snake-like defect domains also have another drawback. These domains persist in the detected crack image giving rise to micron-sized regions of reversed magnetization with resultant lower overall Faraday rotation that is manifested as poor contrast.

It was also observed that areas of film were devoid of defects where a random defect generation method was used. Such areas did not generate a domain wall in the 30 Hz applied field and as a result dead regions occurred in the film. In the course of the development of this process some 200 films were grown and defects introduced by various methods. When selected areas of films worked well, that part of the film was characterized for defect size and density. We thus were able to empirically determine the size and number of defects that produce a good quality, high resolution, good contrast film.

The Defect Criteria

For defects generated at the film-substrate interface, or for defects generated in the bulk of the film, the most preferred defect size is from about 0.8 to about 1.2 μm and number of defects is from about 100 to about 1000 defects/cm². The preferred defect size is from about 0.6 to about 2.0 μm and the preferred number of defects is from about 100 to about 2000/cm². Defect sizes of from about 0.4 to about 1.6 μm and number of defects of from about 100 to about 4000/cm² appear on the evidence to define the operative size, though defect size and distribution outside the extrapolated broad range may provide useful results in accordance with the present invention. Understanding the concept and herein described basis of the invention, optimal and operative ranges for particular epitaxial film and substrate combinations, architectures and usages can be readily determined. For defects at the film surface the size is increased. Where the defects are on the exposed film surface, on present evidence, the most preferred range would be from about 2 to about 3 μm, the preferred range would be from about 2 to about 6 μm and the operable range would be from about 2 to about 8 μm. Here again defect size and distribution outside such range is contemplated by the present invention. Understanding the concept and herein described basis of the invention, optimal and operative ranges for particular epitaxial film and substrate combinations, architectures and usages can be readily determined. The number of defects required at the film surface correspond with the numbers determined to be necessary at the film surface interface. The numerical requirements set forth above assume a random distribution of independent defects, i.e., there are no cases of clustering, overlap, or different types of defects in the same local area.

In designing a film suitable for use in a device for detecting cracks such as described in U.S. Pat. Nos. 4,625,167 and 4,755,752 where visual observation of the switched field corresponding to the detected defect is required, certain film characteristics in addition to the attributes imparted to the magneto-optic films by the present invention are required. Thus, the film before/without imposed defects preferably would have a saturation magnetization 100 gauss to 150 gauss; a switching field of 100–150 gauss with a targeted switching range of from about 2 to about 4 gauss; a magnetic anisotropy preferably in the 2,000 to 6,000 range; and a coercivity as grown of less than about 0.5 oersted. For the as-grown film, the switch field is about equal to the magnetization. The film would need to be thick enough to possess a bistable structure. Thus a minimal thickness of at least about one um would be required for typical magneto-optic film compositions. Below about 1 micron the film would not possess enough Faraday rotation. Moreover, a thickness of less than about 4 $\mu$m is preferred because the films of the present invention at levels above about 4 $\mu$m become too dark to accurately gauge the contrast in switched loci . Moreover, above about 4 $\mu$m the domain structure of the film changes its character from the desired bistable domain structure to serpentine. Although it may be possible for film and crack detector to operate in the transition area between bistable and serpentine domain structure, it is preferred to utilize a film of from about 2 to about 3.5 $\mu$m thickness to assure bistability and adequate contrast in the film at the switching loci indicating the detected cracks.

Among the suitable substrates that may be used in the present invention are the following garnets:

| | |
|---|---|
| GGG | a = 12.383A |
| CMZGGG | a = 12.495A |
| YSGG | a = 12.452 |
| GSGG | a = 12.550 |
| NdGGG | a = 12.510 |
| LaLuG | a = 12.61A |
| SmSGG | a = 12.69 |
| SmGG | a = 12.438 |

Among the films suitable for use in the present invention and on the above substrates are films defined by the following generic formula:

$Bi_xRE_{3-x}Fe_{5-y}Ga_yO_{12}$ where RE represents a rare earth, or combination of rare earths or Y or combination of Y with one or more rare earths.

It is of note that when defect introduction is achieved by annealing, described hereafter in Example II, the film must contain bismuth or an equivalent thereof. It is believed that the large ionic size of Bi at the elevated temperature of annealing has a tendency to form an alternate phase of orthoferrite structure, an alternate structure to that of the garnet and the phase thus formed provides the defect. Alternate ions which can be used to achieve Faraday rotation in lieu of bismuth and likewise form defects because of comparable size include praseodymium and cerium which are the most preferred substitutes.

The film and substrate may be lattice matched or preferably mismatched, with mismatch extending to about 0.03 compression or about 0.01 tension.

The following examples have been selected to illustrate preparation of the films of the present invention utilizing a representative selection of suitable defect forming methods and devices to produce the films of the present invention.

EXAMPLE 1

Laser Ablation

A 3 $\mu$m thick film is grown from a 3kg melt containing the following oxides expressed in weight percent.

| | |
|---|---|
| PbO | 66.19 |
| $Bi_2O_3$ | 27.29 |
| $Fe_2O_3$ | 4.70 |
| $Ga_2O_3$ | 1.02 |
| $V_2O_5$ | 0.45 |
| $Tm_2O_3$ | 0.35 |

The melt is contained in a platinum crucible and initially held at 1000° C. to make sure all the oxides are in solution. The melt is then cooled to 730° C. and a cleaned substrate is horizontally dipped into the melt supported by a platinum holder. The substrate is GGG cut from a boule, polished on (111) faces, so that the final surfaces contain less than 2 defects/cm². The cleaned substrate is a polished GGG wafer which exhibits no scratches or subsurface damage when observed by light microscopy at 200× after etching. The substrate is prepared for examination by etching for 2 rain in 160° C. phosphoric acid to expose defects and residual polishing damage. The substrate is rotated back and forth at 100 rpm reversing rotation direction every five seconds for eight minutes. The film is then pulled out of the melt and the residual melt materials removed by spinning the film horizontally at 300 rpm for five seconds. The film is slowly pulled out of the furnace 5–10 minutes and soaked in 80° C. glacial acetic acid to remove the last traces of flux (5–30 minutes). The reverse side of the film is polished off using colloidal silica and commercially available wafer polishing machine and templates .

The film is then laser ablated using an excimer laser at 248nm. One micron diameter holes are ablated into the film surface in the form of a rectangular array. The holes are spaced on 100 $\mu$m centers. The laser fluence is 10J/cm² and ten laser pulses are required to make each circular ablated hole the right depth to nucleate domain walls without permanently pinning the domain walls. The film is then cleaned in a non-ionic soap solution and rinsed in deionized water. The film (having introduced defects as follows: 1 $\mu$m diameter, 2.5 $\mu$m depth, in square array on 100 $\mu$m centers) is now suitable for .use in an eddy current crack detection device.

The cleaned substrate can be laser ablated on 100 $\mu$m centers before growth in the melt solution. In this case the holes must not be as large or the domains in the grown film will be permanently pinned rendering the film useless. In this case 0.5 $\mu$m diameter holes are ablated into the substrate surface using a wavelength of 248 nm and a single pulse of 10 Joules/cm² fluence. The film is then etched in a 1:3 by volume solution of 31% $H_2O_2$ and concentrated sulfuric acid. The film is etched in this solution at 160° C. for five minutes to first clean the surface of laser ablasion debris and second to enlarge the laser damaged holes to an effective size, A film grown on this substrate will be useful in a crack detection device,

EXAMPLE II

Annealing

Defects can be generated in a post-grown bismuth-containing film by thermal annealing. A film grown on the cleaned substrate described in Example I, and from the melt described in Example I when subjected to a 1050° C. anneal in flowing 0.2 μm filtered oxygen will generate the required size defects in 50 minutes. The defects are related to the formation of an alternate phase of orthoferrite structure, The length of time the film is in the furnace at the annealing temperature is rather critical with an available anneal window of about five minutes. Under-annealed film will exhibit areas which do not switch and can be reclaimed by a further 5–10 minute anneal at 1050° C., If a film is over-annealed the film will switch well but the contrast when viewed through crossed polarizers will be less than adequate. The film in this state cannot be reclaimed by further annealing.

EXAMPLE III

Ion Bombardment

A film is grown on the cleaned substrate described in Example I from the melt described in Example I to a thickness of five microns. The film is subjected to a random ion bombardment in a vacuum chamber, The bombarding 6 Mev gold ions at a cumulative impact density of $1 \times 10^{14}$ impacts/era$^2$ penetrate circa 1 μm into the film leaving a 0.05 μm wide ionization trail. When the outer two micron of film thickness is etched off in 50/50 by volume sulfuric/phosphoric acid at 180° C. the ionization trail is widened to a circa 1 μm wide hole that acts as an effective nucleation site for domain walls rendering the film useful in a crack detection device as well as other devices utilizing magneto-optic films. The film has a defect density of about $10^{33}$/cm$^2$ with defects falling in the 0.8 to 1.2 μm size range.

In a similar fashion the clean substrate of Example I can be subjected to the same 6 Mev gold ion bombardment prior to film growth. In order to enlarge the holes the substrate is etched prior to growth in a 3: I sulfuric acid: 31% hydrogen peroxide solution at 160° C. for five minutes. These enlarged ionization tracks on the substrate should be smaller, suitably about ⅓ smaller in diameter than required to activate the film after growth.

EXAMPLE IV

Particle Deposition

The clean substrate of Example I is prepared for growth by depositing 0.3 μm ceramic particles at a density of 800–1000 particles/cm$^2$ on the surface of the substrate. The substrate is then annealed at 1050° C. for one hour to attach the particles to the subtrate surface by diffusion. Sized alumina particles 0.3 μm in diameter sold pre-sized for polishing purposes work very well and are readily affixed at suitable annealing temperatures of about 1050° C., of the same order as suitable for ceramic particles . For this purpose, 0.001g of 0.3 μm Al$_2$O$_3$ particles are ultrasonically dispersed in 200cc t-butyl alcohol , The substrate is momentarily immersed in the alcohol solution held between 26°–30° C. The substrate is extracted and excess alcohol solution spun off by rapidly spinning the substrate for a few seconds. The substrate is then placed in the cold vapors of liquid nitrogen to freeze the alcohol. The substrate is then placed on a cold copper block in a vacuum chamber at about $1 \times 10^{-3}$ to $1 \times 10^{-4}$ Torr to sublime off the alcohol. As the alcohol is sublimed the particles fall onto the substrate without agglomerating as would happen if the alcohol was simply dried on the substrate. The particles are then diffused lightly onto the surface of the substrate by annealing the substrate for one hour at 1050° C. The resultant film has a defect density of about 700/cm$^2$ with defects of about 1 μm size. When the film growth described in Example I takes place on this pre-"damaged" substrate (defect containing substrate) the resulting film is suitable for use in crack detection devices as well as other devices utilizing magneto-optic films.

EXAMPLE V

Particle Abrasion

The substrate of Example I can be suitably damaged, that is, defects of appropriate size and distribution imposed on the substrate surface, prior to film growth thereon by spraying the substrate with a sized diamond slurry similar to the type sold for the diamond polishing of ceramic petrography samples. A 1 μm diamond spray blown onto the substrate using 50 psi nitrogen works well. The duration of the spray must be determined by trial and error to give a damage/defect density of 800—1000 damaged spots per cm$^2$. In the present Example, duration of 5 second with air brush application suffices. The damaged substrate is then etched in a 3:1 sulfuric acid: 31% hydrogen peroxide mixture for five minutes at 160° C. to enlarge the depth of the subsurface damage. Defects in the range of 0.5 μm to 1.0 μm are formed. At this point observation of the substrate surface with a 200× reflected light microscope can confirm the damage density. If the density is correct the film of Example I can be grown on the damaged surface of the substrate as described in Example I.

Where the film of Example I is grown on the clean substrate of Example I, the film can be activated by the same diamond spray, except this time one micron of film surface is etched off to enlarge the subsurface damage caused by the diamond spray. Etching is effected using 85% H$_3$PO$_4$ for 2 minutes at 185° C. to obtain 2–3 μm diameter defects having a uniform pattern of distribution of about 800–1,000/cm$^2$.

EXAMPLE V I

Laser Ablation Study and Evaluation

A 248 nm KrF excimer laser was used to introduce defects into single crystal GGG substrates and magneto-optic bismuth garnet films. The number, size, and distribution of defects were control led accurately in the 1–100 μm range. Defect introduction raised the coercivity of the films, controlled their switching behavior, and modified the hysteresis loop.

Experimental Procedure

Single crystal magneto-optic garnet films with a (BiTm)$_3$(FeGa)$_5$O$_{12}$ composition were grown by liquid phase epitaxy (LPE) from a PbO-B$_2$O$_3$ flux at 710° C. The films were grown on (111) Gd$_3$Ga$_5$O$_{12}$ (GGG) wafers of 76mm diameter. The measured properties of these films are listed in Table I below for the as-grown condition. The procedures for measurements were those developed for magnetic bubbles and described by Josephs. R. M. Josephs, *Proceeding in the AIP 18th Annual Conference on Magnetism and Magnetic Materials,* 1972, pp. 283–303. The defect densities of the substrate were measured by the etch pit method, D. C. Miller, *J Electrochem, Soc.,* 120, 678 (1973), while those of the film were checked by an AC bias field while viewing between crossed polarizers, E. Heinlein and R. D. Pierce, *IEEE Trans. Mag MAC*-6, 493 (1970). The hysteresis loops were recorded with a vibrating sample magnetometer.

TABLE I

SINGLE CRYSTAL FILM PROPERTIES

| Property | Measured Value |
| --- | --- |
| Film Thickness | 3.0 μm |
| Lattice Constant | 12.391 Å |
| Faraday Rotation | 1.2°/μm @ 633 nm |
| Optical absorption | 800 cm$^{-1}$ @ 633 nm |
| Magnetization | 150 Oe |
| Anisotropy field | 3500 Oe |
| Coercivity | <0.5 Oe |
| Curie temperature | 362 K. |
| Refractive Index | 2.37 @ 633 nm |
| Pinning defect density | <2/cm$^2$ |

Samples of 25mm$^2$ area were cut from a 3 inch film while defects were introduced in other 1cm$^2$ portions. Magnetic parameters were obtained from the hysteresis loops and agreed with those measured without subdividing the initial 76mm diameter film. In order to avoid confusing results from films on both top and bottom GGG substrate surfaces, the bottom film layer was removed by mechanical abrasion and polishing.

Both bare GGG wafers and the magnetic film were processed on an Image Micro System XLR-200, KrF excimer laser operating at 248nm. Some of the specifications for this system are listed in Table II below.

TABLE II

LASER AND SYSTEM SPECIFICATIONS

| Property | Value |
| --- | --- |
| Pulse energy | 140 mJ |
| Pulse duration | 23 ns |
| Maximum average power | 45 W |
| Repetition rate | up to 200 Hz |
| Pulse uniformity | ±5% |
| Target fluence | 18 J/cm$^2$ |
| Beam dimensions at target | 1–500 μm |
| Minimum beam size | 1 × 1 μm$^2$ |
| Stage travel | 15 cm in X, Y |
| Viewing magnification | 360–2000× |
| Energy uniformity at image | ±5% |

The GGG substrate was chosen because defects introduced on it will propagate to the magnetic film during LPE growth. Defect size and depth into the film can be control led by the laser operating conditions. The substrate and film are both garnets but differ in chemical composition. The substrate is optically transparent at 248 nm ($\alpha < 10$cm$^{-1}$) while the film which contains Fe$^{3+}$ has much higher absorption ($\alpha > 1000$cm$^{-1}$). For this reason a particular set of experimental beam parameters was chosen to generate the desired response in film or substrate.

Results

Figures 1A, 1B:
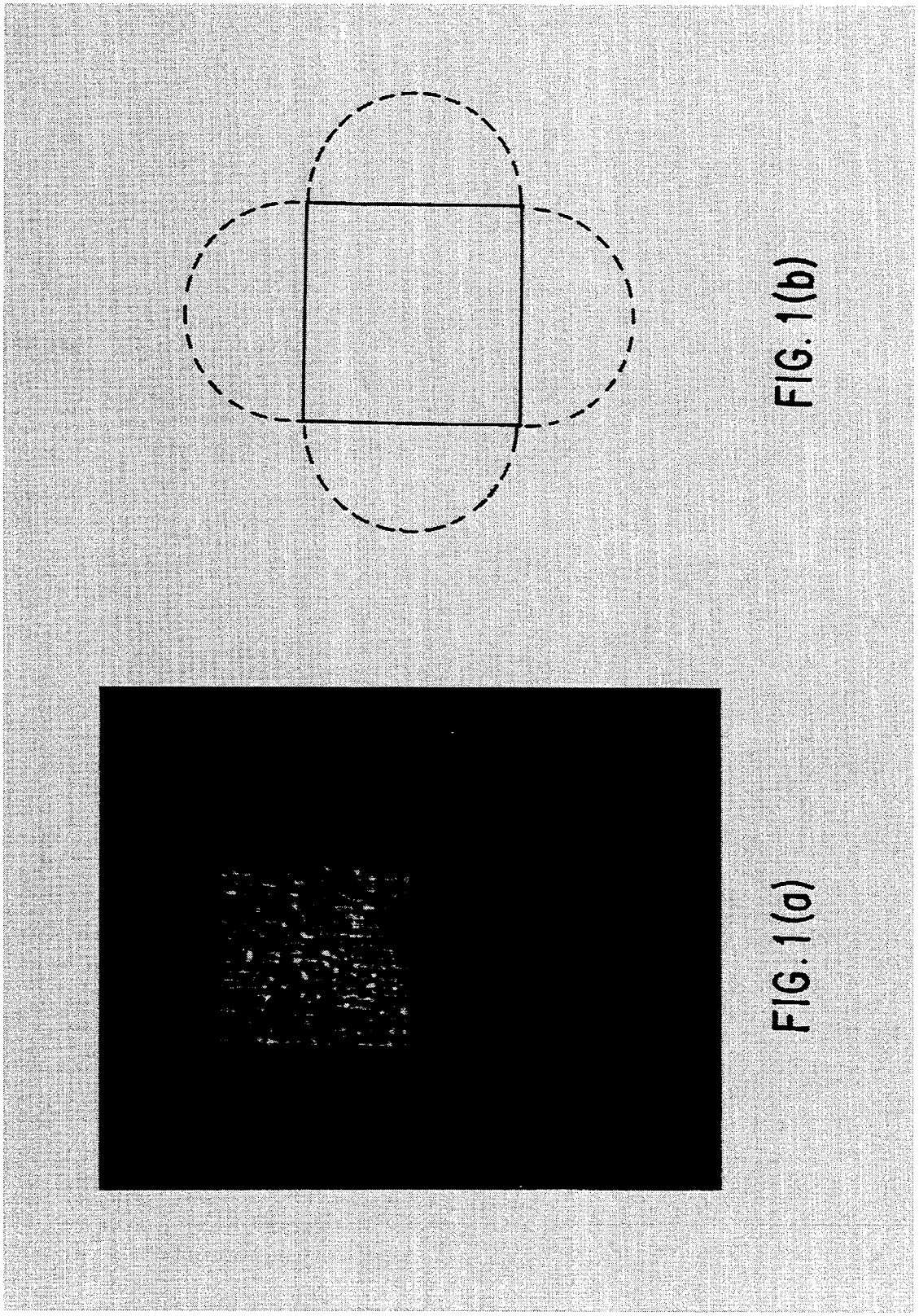
FIG. 1(a) is a photomicrograph of a typical 100 $\mu$m square ablated hole on GGG substrate.
FIG. 1(b) is a schematic drawing of strain field about ablated hole.

The GGG substrate was examined first with 1–100 μm ablations at a fluence of 1.5 J/cm$^2$/pulse at 10 pps using a total of 50 pulses. FIG. 1a. shows a typical 100 μm square ablated hole with sharp material removal. The laser beam also develops a strained area in the bulk garnet which extends out from each side on a semi-circular pattern (see drawing in FIG. 1b.). This was verified by polarized light transmission microscopy in the cubic garnet. We assume the same pattern is obtained for the different size holes. FIG. 1c. shows a portion of 5×5 array of 100 μm ablations of 500 μm centers. The arrays are developed by the X-Y scanning facility on the instrument and each hole was introduced at a fluence of 1.5 J/cm$^2$/pulse with 5–10 pulses at 10 Hz. FIG. 1d. shows two lines of 2 μm width traced at a fluence of 3.56 J/cm$^2$/pulse using 66 pulses at 100 Hz. The above examples exhibit size variation, control of distribution, and pattern flexibility on bare substrates.

Figure 2B:
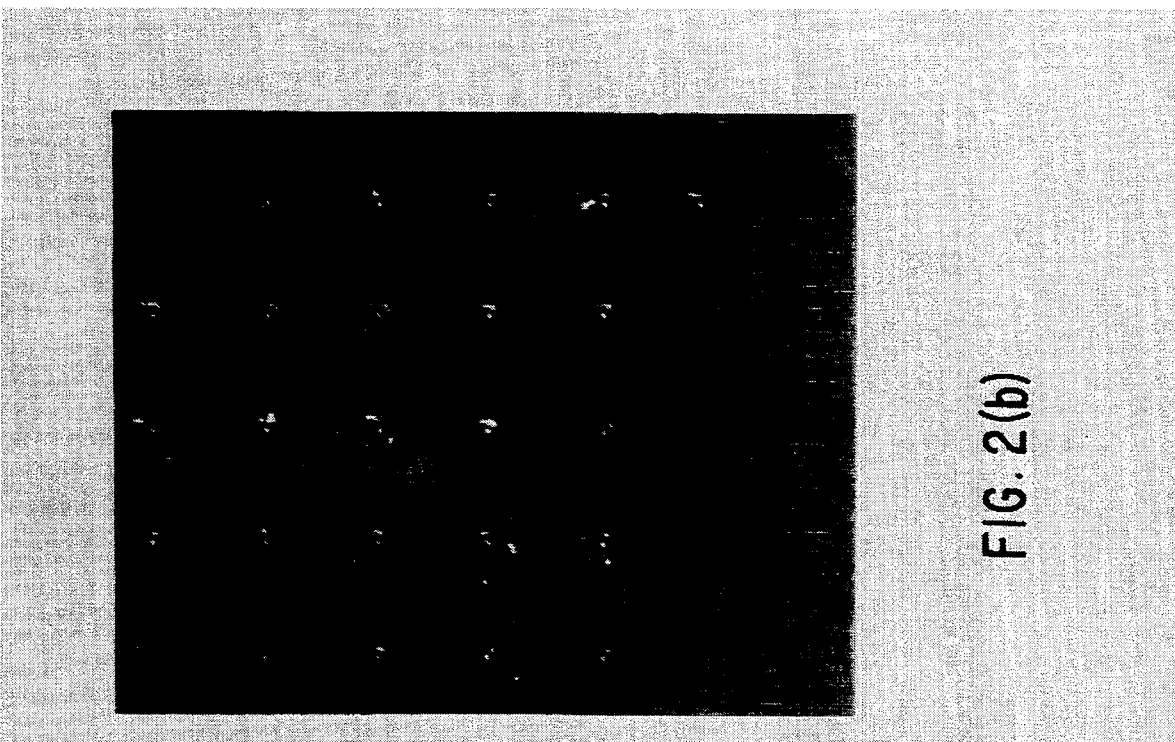
FIG. 2(b) is a photomicrograph of a 5×5 array of 2 $\mu$m holes on 20 $\mu$m centers on bismuth thulium garnet film.
Figure 2A:
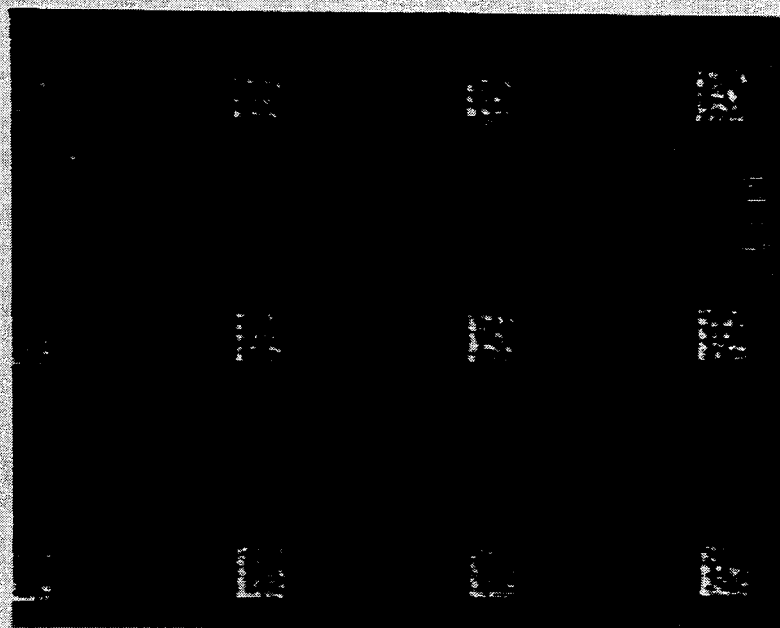
FIG. 2(a) is a photomicrograph of a rectangular array of 25 $\mu$m ablations on 100 $\mu$m centers on film.
Figure 2D:
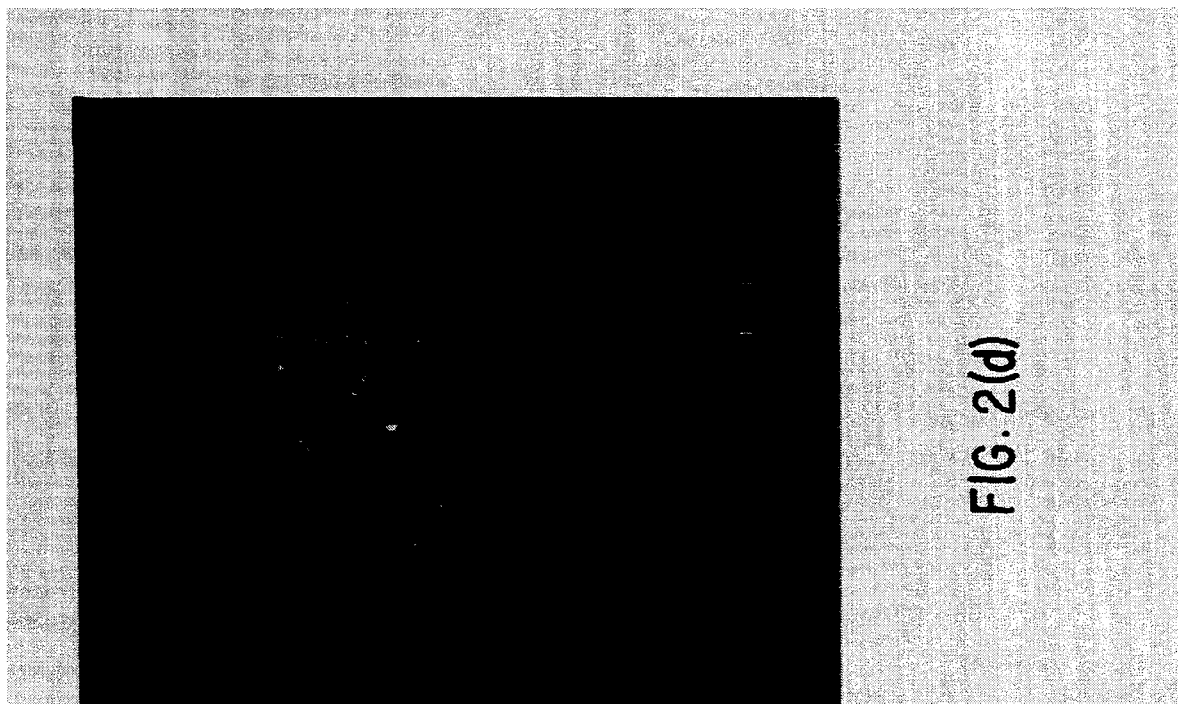
FIG. 2(d) is a photomicrograph illustrating a single 100 $\mu$m ablation on the film with strain pattern.
Figure 2C:
FIG. 2(c) is a photomicrograph illustrating the pinning of magnetic domain at the site of a 1 $\mu$m hole in a 10×10 array spaced on 1mm centers (between crossed polarizers).

In the next experiment the magnetic film was examined first by a matrix array of eight changing fluences from 0.5–12.0 J/cm$^2$/pulse as a function of number of pulses from 1–100. These data were collected for 25 μm ablations and provided a good indication of the film's response, In FIG. 2a, is shown an array of 25 μm ablations which have an estimated depth of >3 μm in the 3 μm film layer . The fluence control and number of pulses can be adjusted to provide only surface damage or a hole through the entire film thickness, The same strained area geometry adjacent to the square hole is found in the film. In FIG. 2b, a 5×5 array of 2 μm ablations of 20 μm centers is registered. The fluence was 11.8 J/cm$^2$/pulse using 10 pulses at 100 Hz. Under these conditions the hole traverses the entire film, A similar 10×10 array of 1 μm ablations on 1mm centers was also inscribed for later magnetic measurements . FIG. 2c. illustrates the pinning of a magnetic domain wall at the site of a 1 μm ablative hole in the 10×10 array of 1mm centers, The domain walls were moved by enclosing the sample in a coil and generating a perpendicular field which was measured with a gaussmeter . Observations were made with the sample between crossed polarizers. In our samples the domain size was several mm$^2$ and wall pinning was observed easily at any of the ablative defects while no pinning occurred at defect-free areas. FIG. 2d. illustrates a single 100 μm hole in the film with surrounding strain field. Lines of 1–100 μm width can also be drawn easily on a film. These are convenient for structuring a large area wafer.

Figure 3:
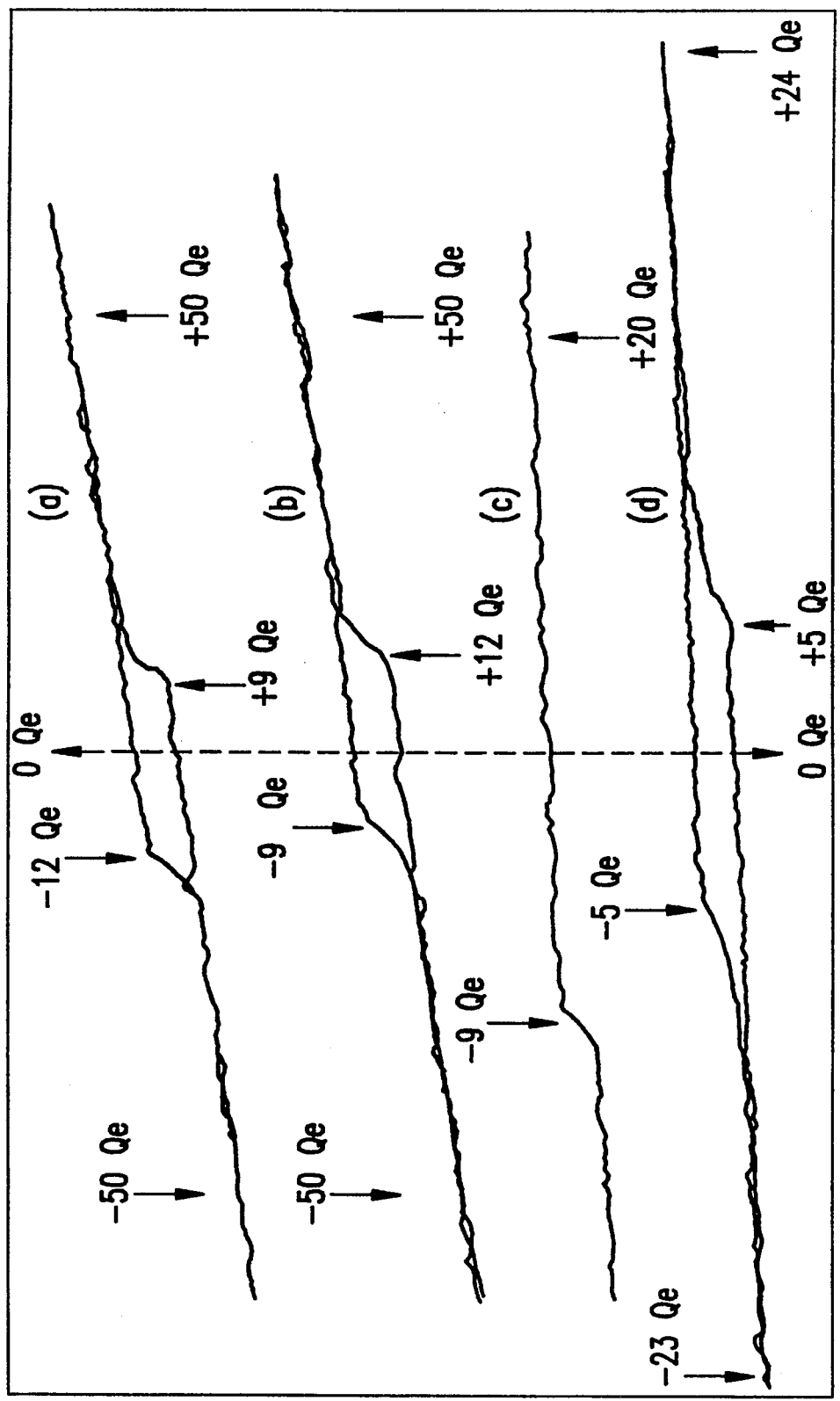
FIG. 3 graphically illustrates hysteresis loops of magnetic film derived from measurement with a vibrating sample magnetometer of square samples measuring 5 to 10 mm on a side. The B–H (hysteresis) loops denominated (a) through (d) representing.

The magnetic film as-grown has a measured coercive field Hc (defined as the minimum field to move a domain wall) of less than a few Oe. This indicated that the film has very few native pinning defects. A brief anneal in O$_2$ above the growth temperature introduces submicron size defects which will begin to increase Hc. FIG. 3 shows a series of magnetic hysteresis loops taken from the same film on which the laser ablations were performed, The measured Hc is variable but in the range of 5–12 Oe. A slight asymmetry is noticed in the + and − directions which is dependent upon the magnetic prehistory of the sample. At the 10×10 array of 1 μablations located on 1mm centers, a direct measurement of Hc from domain wall pinning and unpinning was 10 Oe, At the 25 μm ablations about 1mm apart, Hc increased to 16 Oe, Finally at the 5×5 array of 2 μm ablations located on 20 μm centers, Hc increased to 22 Oe. The hysteresis curve has a nearly square shape with fairly long "tails." This type of curve is ideal for good switching and data retention, The "switch" fields are low and can be controlled quite accurately by the defect size and particularly their distribution. The loop tails are believed to arise from small wall segments which are pinned hard enough for increasing drive fields to dislodge.

The relationship of coercivity to film perfection has been investigated for many polycrystalline films such as Mn Bi and recently the garnets, K. Odagawa, K. Nakagawa and A. Itoh, *IEEE Trans. Mag.* MAG-26, 1721 (1990). Unfortunately these films have grain sizes of the order of 0.1–5.0 μm and hence coercivity as high as 200–1000 Oe. Most experiments relate coercivity to film thickness or sample size, G, Vertesy, M, Pardavi-Horvath, I. Tomas and L. Pust, *J. Appl. Phys.* 63, 1694 (1988). The theory of Trauble, H. Trauble in "Modern Problems of Metal Physics" Edited by A. Seeger (Springer, New York, 1966) Vol. 2 Eq 8.19., which arises from dislocations, predicts that Hc is proportional to $d^{\frac{1}{2}}$ where d is the planar density of obstacles. The obstacle size is assumed about equal to a domain wall width which for our garnets is estimated at 0.4 μm. However, no consideration is given to the average distance between obstacles. The Trauble theory does not hold for our coercivity range and defect density. The more recent theory of Mansuripur, M. Mansuripur, *J Appl. Phys.* 53, 1660 (1982), offers a mathematical description predicting general shapes of hysteresis loops (see FIG. 6). The mathematical description of predicting general shapes of hysteresis loops in Mansuripur provides the most accurate mathematical model describing hysteresis loops observed in films of the present invention.

Laser ablation was found to provide a tool to introduce bulk defects into substrates or magnetic films. Fine control on the density and geometric distribution of defects is attainable. These defects can be readily introduced in films ranging in thickness from about 2 to about 4 μm. The defects assist coercivity control. In different magnetic devices where switching is important, such as optical isolators, microwave devices and sensors, coercivity in a predetermined range, e.g., about 1 to about 50 Oe, can be achieved by the controlled introduction of defects.

The films of the present invention find utility and can be advantageously used in devices other than sensing and/or imaging of magnetic fields or currents where the film typically is in the form of a contiguous layer.

The film of the present invention can be used to produce pixel arrays suitably by subdividing the film into separate pixels utilizing photolithography and chemical etching in accordance with the commonly used procedures of the art. The films of the present invention, thus, may be used in the manufacture of pixel arrays as described in U.S. Pat. No. 4,625,390 among others. The pixel array where the films of the present invention are used has the advantage that the current required to generate the switching field is lower by an order of magnitude to the switching current required to generate the switching field in the pixels formed previously using switching films of the prior art.

The films of the present invention are also useful in microwave signal processing devices and also magneto-optic light deflectors where substitution of the films of the present invention for epitaxial films of the prior art possessing switchable states of magneto-optic rotation allows operation at a switching field substantially lower than that required in devices utilizing films of the prior art, Magneto-optic light deflectors and microwave signal processing devices in which the films of the present invention are suitably used are described in U.S. Pat. No. 4,625,390.

Referring to FIG. 5, the material being tested 250 is shown with crack 251. The magneto-optic sensor film 210, with a light reflector 212 adjacent to the exposed surface thereof is placed on material 250 to be tested for defects, i.e., cracks, pits and corrosion, As shown, the magneto-optic film 210 is supported on substrate 211. The film 210 typically of a thickness in the range of from about 2 to 3 microns is supported on an optically transparent non-magnetic single crystal garnet substrate 211 of adequate thickness to provide mechanical stability. Typically, the combined thickness of film 210 and substrate 211 is from about 400 to 500 microns, The light reflector 212 sandwiched between the test material 250 and magneto-optic film 210 suitably is a copper film of 100 micron thickness with diffuse reflective surface facing the film 210 which serves to reflect polarized light to the detector 230. The light reflector 212 may also be formed of silver, gold and other metals provided only that such material be electrically conductive and have a diffuse reflective surface. The light reflector 212 serves to introduce an eddy current in the test sample. The light source 240 is an unpolarized light emitting diode. The light is directed through a dichroic sheet polarizer 260. The reflected light is directed through analyzer 270 composed of the same material as polarizer 260 with orientation of analyzer 270 with respect to polarizer 260 set to optimize observed image contrast.

In FIG. 6, a microwave signal processing unit is schematically illustrated. A microwave source 101 providing gigahertz ($GH_z$) frequency radiation denoted by numeral 111 is utilized as an input to an acousto-optic Bragg cell 102. Laser light 112 from laser light source 103 is diffracted through the acousto-optic Bragg cell crystal as a function of the microwave frequency and amplitude, A detector/receiver 106 is situated to receive light 112 which has passed through acousto-optic Bragg cell device 102. Chip 10, comprising a plurality of independently switchable pixels (see FIG. 9 for detail) is interposed between acousto-optic Bragg cell device 102 and detector/receiver 106. The detector/receiver 106 may comprise a photocell or photodiode converting light to an electrical signal which can be analyzed to characterize amplitude and frequency of the microwave signal. Chip 10 can be used to block or pass portions of the light passing through Bragg cell device 102. In detector 106, signals are separated as a function of microwave frequency. As is apparent, chip 10 functions as Fresnel or Fourier transformer of the input amplitude. Lens 104 intermediate the acousto-optic Bragg cell 102 and chip 10 and lens 105 intermediate chip 10 and detector/receiver 106 are used to focus and direct the image carrying laser light to the chip and detector/receiver respectively. Specific applications of the signal processing unit include RF spectrum analysis, pattern recognition and signal blocking/filtering.

In FIG. 7, a magneto-optic light deflector is illustrated. In this embodiment of the invention the epitaxial layer 121 comprises parallel linear arrays of the epitaxial film 122 arranged either contiguous to one another or with an intervening space 123 therebetween. The aligned parallel stripes of magneto-optic film 122 are supported on a non-magnetic monocrystalline garnet substrate 120. In the drawing $d_1$ and $d_2$ are used to denote the periodic striped domains formed by the aligned parallel strips of film 122 and the intervening spaces between such parallel striped domains respectively. The intervening spaces may be light transmitting or may be made light reflecting/absorbing/blocking. Indeed where spaces are not light transmitting the switching circuitry for the parallel strips may be carried in such spaces, e.g., the spaces $d_2$ may be filled in with a conductor which blocks the passage of light. The arrows placed within the forward end of the parallel strips of film are used to denote the direction of oppositely magnetized domains.

Polarized light, generally introduced at an angle relative to the surface of the parallel linear epitaxial stripes and substrate, is diffracted as a consequence of periodic variations in amplitude or phase of such incoming light. The domain arrays introduce a periodic 180° phase change through magnetic birefringence. The light passing through the substrate in turn is passed through the analyzer 124.

As with other illustrated arrangements utilizing the switchable magneto-optic elements of the present invention, it is possible to use a bias field to enhance switching by reducing the demands on the magnetic field generated by the conductors utilized for switching.

Magneto-optic light deflectors utilizing the magneto-optic elements of the present invention can be used for light deflection switching lens formation and image processing where operated in the transmissive mode.

The arrangement of FIG. 7 can be used in either the transmissive or reflective mode. In the reflective mode the Kerr effect is utilized.

The composite of the present invention is suitable for use in magneto-optic chips and displays.

A typical chip is shown in simplified form in FIGS. 8 and 9. The chip, generally indicated as 10, comprises the substrate of the invention 12 having the film of the invention 14 on its surface. The magnetized film imposes the Faraday effect on polarized light passing therethrough, The film 14 is divided into individual pixel areas or posts 16. Typically, the posts 16 are laid out in a rectangular pattern of columns and rows such as those in FIG. 8 labeled for convenience as $CC_1$-$CC_6$ (for column 1 through column 6) and $CR_1$-$CR_6$ (for row 1 through row 6, respectively). A series of row control wires 18 and column control wires 20 are disposed between the posts 16 as shown in FIG. 8.

To make the composite of the invention into a chip, the exposed surface of the epitaxial film is just coated with $SiO_2$ (top only) by chemical vapor deposition (CVD) at 725° C. or lower. Photoresist is placed on top of the $SiO_2$ coating. The photoresist is exposed through a mask that defines the pixels. The photoresist and $SiO_2$ are etched through where exposed. Exposed garnet is etched with $H_3PO_4/H_2SO_4$, 50/50 by volume at a temperature of about 150° C. The remaining $SiO_2$ is removed with HF. Then a gold layer is placed over the pixel surface. Thereafter the pattern for ion implant is: Ne+1 at 200 Kev $4-5\times10^{13}$ ions/sq. cm. Where a strain gradient is desired multiple implants may be used. The gold is removed and a new layer of gold layed down to pattern for the first drive line. Then a layer of polymide is put on top for insulation and the second conductor is put down. Finally paths are opened in the first drive line layer so connectors can be made. After testing for continuity of resistive bonding to an outside drive circuit can be effected.

For convenience, the row control wires 18 are located as CR1-CR6 (for control row) while the column control wires 20 are similarly labeled CC1-CC6 (for control column). The single post (pixel) 16 for column 1, row 1 (C1, R1) is shown greatly enlarged in FIG. 9. By control of the current direction in CR1 and CC1, the film 14 of the post 16 of FIG. 9 can be magnetized into the post 16 as FIG. 9 is viewed or magnetized out of the post 16 of FIG. 9 as it is viewed.

In FIG. 10, a typical display system incorporating the chip 10 of FIG. 8 is indicated as 23. Chip 10 is placed between a polarizer 22 and a polarization analyzer 24. The wires 18 and 20 used to address the chip 10 are contained within the cable 26 connecting the chip 10 to the display driver 28. The display drives 28 directs current through the wires 18, 20 so as to magnetize the various posts (pixels) 16 in a manner to effect a display pattern throughout the posts 16 of chip 10. Light 30 passing through the polarizer 22 is polarized by the Faraday effect according to the display pattern impressed into the posts 16 of chip 10 by the display driver 28. Light 30 then passes through the polarization analyzer 24. The amount of light passing through the analyzer 24 is a function of the $\cos^2 \theta$ of the angle $\theta$ of polarization of the light 30 with respect to the polarization axis of the analyzer 24.

The fast switchable material of the present invention, most suitably in the form of a wafer having a plurality of pixels preferably of 25–100 μm size, can be used in a line or page printer to form an image on a suitable recording medium. The recording medium may be thermographic paper. Alternatively, the image may be projected upon a thermomagnetic recording medium so as to induce the thermomagnetic sensitive medium a retained pattern corresponding to the image pattern. From the thermomagnetic recording medium, the retained pattern may be transferred to a further recording medium by the process of magneto-xerography.

As will be noted at once, the image forming system of the invention, when used in an optical printer, obviates the need for character masks, and switches generally required in the optical printers of the prior art.

In the embodiment of the invention shown in FIG. 11, the drum 50 having a thermomagnetic sensitive surface accepts image 30. The diameter of the drum should be large enough relative to the projected image to accept the image directly without distortion, otherwise a distortion correcting lens 35 may be interposed in the optical path between the image forming system 23 and the drum thermomagnetic recording surface . The thermomagnetic recording arrangement includes the drum 50 which is driven by a suitable rotational drive mechanism (not shown) counterclockwise about axis 60. Disposed adjacent to drum 50 is a premagnetizing head 51, suitably a retractable permanent magnet or d.c. electromagnet which magnetizes the magnetic material of the thermomagnetic sensitive surface of drum 50. An appropriate temperature bias source, such as a heating lamp, positioned adjacent premagnetizing head 51 or located within drum 50, may be provided. A suitable erase head 52 is disposed clockwise of premagnetizing head 51 to controllably erase any magnetic image stored on drum 50, so that a new image may be recorded. Light 30 from image forming system 23 passes through corrective optics 35, impinges at surface area 40 and thermomagnetically induces an image corresponding to the pattern on chip 10 of image forming system 23 in the sensitive recording surface of the drum 50. The magnetic image stored on drum 50 then passes a magnetic toner applying element 53, such as described, e.g., in U.S. Pat. No. 3,698,005. Excess toner is removed by a suitable air knife. The toner image is conveyed to an image transfer mechanism including a paper source drum 54, resilient pressure roller 55, and take-up drum 56. Drum 54 and roller 55 rotate in a clockwise direction while take-up drum 56 rotates in a counterclockwise direction. Transfer of the toner image on drum 50 to paper 61 takes place as the paper 61 travels over roller 55 at which time it is brought into contact with the surface of drum 50. After one complete copy of the image pattern stored in drum 50 has been transferred to paper 61, a suitable toner remover mechanism 57, such as rotary bristle brush, removes toner particles not transferred to paper 61 to clean the surface of the drum. The image pattern is erased by erase head 52 to prepare the drum to receive a new thermomagnetically induced image.

The detailed description set forth is the preferred embodiment of the method of the present invention. However, certain changes may be made in carrying out the above method without departing from the scope of the invention; it is therefore intended that all matter contained in the above description shall be interpreted as illustrative and not in a limited sense. It is also to be understood that the following claims are intended to cover all of the generic and specific features of the invention herein described, and all statements of the scope of the invention, which as a matter of language, might be said to fall therebetween, In the claims:

1. A bistable single crystal magneto-optic film of a thickness of about 1 $\mu$m to about 4 $\mu$m, said film being deposited on a substrate, said film and substrate having a maximum mismatch of about 0.03Å in a compression or about 0.01Å in tension, said film being of preselected coercivity and having induced defects distributed therein, the size of said defects being from about 0.4 $\mu$m to about 4.0 $\mu$m and the number of said defects per cm$^2$ being within the range of from about 10 to about 10$^6$.

2. The bistable single crystal magneto-optic film of claim 1, wherein the defect size is from about 0.6 $\mu$m to about 2.0 $\mu$m and the number of defects per cm$^2$ is within the range of from about 10$^2$ to about 10$^4$.

3. The bistable single crystal magneto-optic film of claim 1, wherein the defect size is from about 0.8 $\mu$m to about 1.2 $\mu$m and the number of defects per cm$^2$ is within the range of from about 100 to about 1000.

4. A bistable single crystal magneto-optic film of a thickness of about 1 $\mu$ to about 4 $\mu$, said film being deposed on a substrate, said film and said substrate having a maximum mismatch of about 0.03Å to compression or about 0.01Å in tension, said film being of coercivity in the range of from about 1 Oe to about 50 Oe having induced defects distributed therein, the size of said defects being from about 0.8 $\mu$m to about 1.2 $\mu$m and the number of said defects per square centimeter being within the range of from about 100 to about 1,000.

5. The bistable single crystal magneto-optic film of claim 4, wherein the coercivity is less than about 10 Oe.

6. The bistable single crystal magneto-optic film of claim 5, wherein the coercivity is from about 1 to about 10 Oe, the anisotropy is from about 1,000 to about 6,000 G, the switch field is from about 1 to about 10 Oe and the saturation magnetization is from about 100 to about 150 gauss.

7. In a pixel array comprising a subdivided single crystal magneto-optic film deposited on a substrate, the improvement comprising utilizing a bistable single crystal magneto-optic film of a thickness of about 1 $\mu$ to about 4 $\mu$, said film and said substrate having a maximum mismatch of about 0.03Å in compression or about 0.01Å in tension, said film being of preselected coercivity having induced defects distributed therein, the size of said defects being from about 0.4 $\mu$m to about 40 $\mu$m and the number of said defects per cm$^2$ being within the range of from about 10 to about 10$^6$.

8. The pixel array of claim 7, wherein the defect size is from about 0.6 $\mu$m to about 2.0 $\mu$m and the number of defects per cm$^2$ is within the range of from about 10$^2$ to about 10$^4$.

9. The pixel array of claim 7, wherein the coercivity is in the range of from about 1 Oe to about 10 Oe and the defect size is from about 0.8 $\mu$m to about 1.2 $\mu$m and the number of defects per cm$^2$ is within the range of from about 100 to about 1,000.

10. In an apparatus for detecting and providing images of flaws, voids, discontinuities, or the like in a target material by observing magnetic field pertubations in a magnetic material the improvement which comprises utilizing as said magnetic material a bistable single crystal magneto-optic film of a thickness of about 1 $\mu$m to about 4 $\mu$m, said film being deposited on a substrate, said film and substrate having a maximum mismatch of about 0.03Å in compression or about 0.01Å in tension, said film being of preselected coercivity and having induced defects distributed therein, the size of said defects being from about 0.4 $\mu$m to about 4.0 $\mu$m and the number of said defects per cm$^2$ being within the range of from about 10 to about 10$^6$.

11. The flaw detecting and imaging apparatus of claim 10, wherein the defect size is from about 0.6 $\mu$m to about 2.0 $\mu$m and the number of defects per cm$^2$ is within the range of from about 10$^2$ to about 10$^4$.

12. The flaw detecting and imaging apparatus of claim 10, wherein the coercivity is in the range of from about 1 Oe to about 10 Oe and the defect size is from about 0.8 $\mu$m to about 1.2 $\mu$m and the number of defects per cm$^2$ is within the range of from about 100 to about 1,000.

13. The flaw detecting and imaging device of claim 12, wherein the coercivity is in the range of from about 2 Oe to about 6 Oe.

14. The flaw detecting and imaging apparatus of claim 12, wherein the magneto-optic film has a saturation magnetization of from about 100 gauss to about 150 gauss and an anisotropy field of from about 1,000 to about 6,000 G.

15. The flaw detecting and imaging apparatus of claim 13, wherein the magneto-optic film has a saturation magnetization of from about 100 gauss to about 150 gauss and an anisotropy field of from about 1,000 to about 6,000 G.

16. The flaw detecting and imaging apparatus of claim 15, wherein the film thickness is from about 2 to about 3.5 $\mu$m.

17. In a microwave signal processing unit including a Fresnel or Fourier transformer comprised of a pixel array of independently switchable pixels of magneto-optic film the improvement which comprises utilizing as said pixel array a subdivided bistable single crystal magneto-optic film of a thickness of about 1 $\mu$m to about 4 $\mu$m, said film being deposited on a substrate, said film and substrate having a maximum mismatch of about 0.03Å in compression or about 0.01Å in tension, said film being of preselected coercivity and having induced defects distributed therein, the size of said defects being from about 0.4 $\mu$m to about 0.4 $\mu$m and the number of said defects per cm$^2$ being within the range of from about 10 to about 10$^6$.

18. The microwave signal processing unit of claim 17, wherein the bistable single crystal magneto-optic film has a coercivity in the range of from about 1 Oe to about 50 Oe, the size of the defects in said film is from about 0.8 $\mu$m to about 1.2 $\mu$m and the number of said defects per square centimeter is within the range of from about 100 to about 1,000.

19. The microwave signal processing unit of claim 18, wherein the bistable single crystal magneto-optic film has a coercivity less than about 10 Oe.

20. The microwave signal processing unit of claim 19, wherein the bistable single crystal magneto-optic film has a coercivity of from about 1 to about 10 Oe, an anisotropy of from about 1,000 to about 6,000 G, a switch field of from about 1 to about 10 Oe and a saturation magnetization of from about 100 to about 150 gauss.

21. In a magneto-optic light deflector, the improvement which comprises utilizing as the magneto-optic element therefor a bistable single crystal magneto-optic film of a thickness of about 1 μm to about 4 μm, said film being deposited on a substrate, said film and substrate having a maximum mismatch of about 0.03Å in compression or about 0.01Å in tension, said film being of coercivity in the range of from about 1 Oe to about 50 Oe and having induced defects distributed therein, the size of said defects being from about 0.8 μm to about 1.2 μm and the number of said defects per square centimeter being within the range of from about 100 to about 1,000.

22. The magneto-optic light deflector of claim 21, wherein the coercivity is less than about 10 Oe.

23. The magneto-optic light deflector of claim 22, wherein the coercivity is from about 1 to about 10 Oe, the anisotropy is from about 1,000 to about 6,000 G, the switch field is from about 1 to about 10 Oe and the saturation magnetization is from about 100 to about 150 gauss.

24. In the manufacture of a magneto-optic monocrystalline film of a thickness of about 1 μm to about 4 μm, said film being deposited on a substrate, said film and substrate having a maximum mismatch of about 0.03Å in compression or about 0.01Å in tension, the improvement which comprises inducing defects in said film of size within the range of from about 0.4 μm to about 4.0 μm and distribution within the range of from about 10 to about $10^6$ per $cm^2$ for form a bistable magneto-optic film of preselected coercivity in the range of from about 1 to about 50 Oe.

25. The improved method of manufacture of claim 24 further characterized in that the defect size is from about 0.6 μm to about 2.0 μm and the number of defects per $cm^2$ is within the range from about $10^2$ to about $10^4$.

26. The improved method of manufacture of claim 24 further characterized in that the defect size is from about 0.8 μm to about 1.2 μm and the number of defects per $cm^2$ is within the range of from about 100 to about 1,000.

27. The method of claims 24, 25 or 26, wherein said magneto-optic monocrystalline film is an epitaxial film formed on a monocrystalline garnet substrate and said defects in said monocrystalline film are induced by (a) mechanical abrasion of the substrate followed by (b) formation of said monocrystalline film on the abraded surface of said substrate.

28. The method of claims 24, 25 or 26, wherein said magneto-optic monocrystalline film is an epitaxial film formed on a garnet substrate and said defects in said film are induced by mechanical abrasion of the exposed surface of said monocrystalline film.

29. The method of claims 24, 25 or 26, wherein said magneto-optic monocrystalline film is an epitaxial film formed on a monocrystalline garnet substrate and said defects in said film are induced by (a) particle deposition on the surface of the substrate, followed by (b) heating of the substrate surface to cause decomposition or diffusion of the particles at said substrate surface to form defects at said substrate surface in turn followed by (c) formation of said monocrystalline film on the surface of said substrate.

30. The method of claims 24, 25 or 26, wherein said magneto-optic monocrystalline film is an epitaxial film formed on a monocrystalline garnet substrate and said defects in said film are induced by (a) particle deposition on the exposed surface of said monocrystalline film after formation of said monocrystalline film on said monocrystalline garnet, followed by (b) heating the exposed surface of the film to cause decomposition or diffusion of the particles at said film surface.

31. The method of claims 24, 25 or 26, wherein said magneto-optic monocrystalline film is an epitaxial film formed on a monocrystalline garnet substrate and said defects in said film are induced by (a) heavy ion impingement of the substrate followed by (b) formation of an epitaxial film of said monocrystalline film on the abraded surface of said substrate.

32. The method of claims 24, 25 or 26, wherein said magneto-optic monocrystalline film is an epitaxial film formed on a monocrystalline garnet substrate and said defects in said film are induced by (a) heavy ion impingement of the substrate followed by (b) chemical etching to increase the size of defects formed by heavy ion impingement in turn followed by (c) formation of said monocrystalline film on the abraded surface of said substrate.

33. The method of claims 24, 25 or 26, wherein said magneto-optic monocrystalline film is an epitaxial film formed on a monocrystalline garnet substrate and said defects in said film are induced by heavy ion impingement of the exposed surface of said film.

34. The method of claims 24, 25 or 26, wherein said magneto-optic monocrystalline film is an epitaxial film formed on a monocrystalline garnet substrate and said defects in said film are induced by (a) heavy ion impingement of the exposed surface of said film on said monocrystalline garnet followed by (b) chemical etching to increase the size of defects formed by heavy ion impingment.

35. The method of claims 24, 25 or 26, wherein said magneto-optic monocrystalline film is an epitaxial film formed on a monocrystalline garnet substrate and said defects in said film are induced by (a) laser ablation of the substrate followed by (b) formation of an epitaxial film of said monocrystalline film on the abraded surface of said substrate.

36. The method of claims 24, 25 or 26, wherein said magneto-optic monocrystalline film is an epitaxial film formed on a monocrystalline garnet substrate and said defects in said film are induced by laser ablation of the exposed surface of said film.

* * * * *